US005681696A

United States Patent [19]

Wang

[11] Patent Number: 5,681,696
[45] Date of Patent: *Oct. 28, 1997

[54] SYNTHETIC PEPTIDE COMPOSITIONS WITH IMMUNOREACTIVITIES TO ANTIBODIES TO HTLV

[75] Inventor: Chang Yi Wang, Great Neck, N.Y.

[73] Assignee: United Biomedical, Inc., Hauppauge, N.Y.

[*] Notice: The term of this patent shall not extend beyond the expiration date of Pat. No. 5,476,765.

[21] Appl. No.: 457,865

[22] Filed: Jun. 1, 1995

Related U.S. Application Data

[60] Division of Ser. No. 901,874, Jun. 22, 1992, Pat. No. 5,476,765, which is a continuation-in-part of Ser. No. 469,291, Jan. 24, 1990, abandoned, which is a continuation-in-part of Ser. No. 297,635, Jan. 13, 1989, abandoned, which is a continuation-in-part of Ser. No. 1,885, Jan. 9, 1987, Pat. No. 4,833,071.

[51] Int. Cl.$^6$ .................................................. C12Q 1/70
[52] U.S. Cl. ............................... 435/5; 435/974; 530/325
[58] Field of Search ........................... 435/5, 974; 530/325

[56] References Cited

U.S. PATENT DOCUMENTS

| | | | |
|---|---|---|---|
| 4,735,896 | 4/1988 | Wang et al. | 435/5 |
| 4,833,071 | 5/1989 | Wang et al. | 435/5 |
| 4,879,212 | 11/1989 | Wang et al. | 435/5 |
| 5,066,579 | 11/1991 | Reyes | 435/5 |
| 5,194,586 | 3/1993 | Maeda et al. | 530/324 |
| 5,378,805 | 1/1995 | Lal | 530/326 |
| 5,516,632 | 5/1996 | Palker et al. | 435/5 |

FOREIGN PATENT DOCUMENTS

| | | | |
|---|---|---|---|
| WO 8601834 | 3/1986 | WIPO | C12Q 1/70 |
| 89/06543 | 7/1989 | WIPO | A61K 39/12 |

OTHER PUBLICATIONS

B.J. Poiesz., et al., Proc. Natl Acad. Sci. USA., 77:7415–19 (1980).
B.J. Poiesz., F.W. Ruscettti, M., S. Reitz., V. S. Kalyanaraman, R. Gallo, Nature (London) 294:268–71 (1981).
R.C. Gallo et al., Proc. Natl. Acad. Sci. USA., 79:5680–83 (1982).
M. Essex at al., Science, 221: 1061–63 (1983).
P. Clapham, K. Napy, R. A. Weiss, Proc. Natl. Acad. Sci. 81:2886–89 (1984).
R.C. Gallo et al., Cancer Res., 43:3892–99 (1983).
M.S. Reitz and R.C. Gallo, Cancer Surveys, 4:313–29 (1985).
W.A. Blattner, K. Tokatsuki, R. C. Gallo, J. Am. Med. Assoc., 250:1074–80 (1983).
K. Takatsuki, J. Uchiyama, K. Sagawa, J. Yodoi, Topics in Hematology, S. Seno, F. Takaku, S. Irino, Eds. (Excerpta Medica, Amsterdam, 1977) pp. 73–77.
W. A. Blattner et al., Int. J. Cancer, 30:257–64 (1982).
D. Catovsky et al., Lancet, 1982, 639–43 (1982).
D. W. Blayney et al., J. Am. Med. Assoc., 250:1048–52 (1983).
M. Robert–Guroff, F. W. Ruscetti, L. W. Posner, B. J. Poiesz, R.C. Gallo, J. Exp. Med., 154:1957–64 (1981).
R.C. Gallo et al., Proc. Natl. Acad. Sci. USA., 79:5680–83 (1981).
M. Robert–Guroff et al., J. Exp. Med., 157:248–58 (1983).
M. Shimoyama et al, Jpn. J. Clin. Oncol., 12:109–16 (1982).
M. Seiki, S. Hattori, Y. Hirayama, M. Yoshida, Proc. Natl. Acad. Sci. USA., 80:3618–22 (1983).
Saxinger, C.W. et al., Science, 225:1473–76 (1984).
Samuel, K.P. et al., Science, 226:1094–97 (1984).
Wang, J.J–G, Steel, S., Wisniewolski, R. and Wang, C.Y., Proc. Natl. Acad. Sci. USA, 83:6159–63 (1986).
Liu, Fu–Tong et al., Biochemistry, 18:690–97 (1979).
V. S. Kalyanaraman, M. G. Sarngadharan, M. Robert–Guroff et al., Science, 218:571–73 (1982).
J. D. Rosenblatt et al., N. Engl. J. Med., 315:372–77 (1986).
M. Robert–Guroff, S. H. Weiss, J. H. Giron et al., J. Am. Med. Assoc., 255:3133–37 (1986).
H. Lee, P. Swanson, V. S. Shorty et al., Science, 244:471–75 (1989).
R. C. Gallo, Med. Oncol. Tumor Pharmacother., 3:265–67 (1986).
K. Shimotohno, Y. Takahashi, et al., Proc. Natl. Acad. Sci. USA., 82:3101–05 (May 1985).
J. Sodroski, R. Patarca, D. Perkins et al., Science, 225:421 (1984).
G. M. Shaw, M. A. Gonda, G. H. Flickinger et al., Proc. Natl. Acad. Sci. USA., 81:4544–48 (1984).
S. G. Sandler, C. Fang, in Transfusion–Transmitted Viral Disease, Arlington, VA:American Assn. of Blood Bankers, pp. 19–35 (1987).

Primary Examiner—Christine M. Nucker
Assistant Examiner—Jeffrey Stucker
Attorney, Agent, or Firm—Morgan & Finnegan, LLP

[57] ABSTRACT

The present invention relates to a method for the detection HTLV-I and/or HTLV-II reactive antibodies and diagnosis of ATL (adult T cell leukemia/lymphoma) condition by the use of chemically synthesized peptide compositions. The peptide compositions comprise peptides having amino acid sequences corresponding to transmembrane and external segments of the envelope protein of HTLV-I/HTLV-II and mixtures thereof. The peptide compositions are highly immunoreactive with antibodies to HTLV in sera. The present invention further relates to a method for the simultaneous detection and diagnosis of ATL, HTLV-I and/or HTLV-II infection and Acquired Immune Deficiency Syndrome (AIDS) by the use of chemically synthesized HTLV peptide compositions in conjunction with a chemically synthesized HIV (1 and 2) peptide composition. The present invention also provides a simple method to differentiate between HTLV-I and HTLV-II infections.

The detection method includes an enzyme-linked immunosorbent assay (ELISA), an immunoradiometric assay (IRMA), and other forms of immunoassay procedures such as enzyme immuno blotting assay on nitrocellulose paper and an agglutination assay using the peptide composition as the antigen. The preferred detection method is ELISA.

3 Claims, 7 Drawing Sheets

FIG. 1-1

```
HTLV-1  MG KFLAT L I L FFQ F CPLI F GDYSP S C CTLT I G V SSYHS K PC N P A QPVC S W T LDL LA L SA DQ A L Q PPCPNL VS
HTLV-2  MG NVFF - L L L --- F SLTH F PLAQQ S R CTLT V G I SSYHS S PC S P T QPVC T W N LDL NS L TT DQ R L H PPCPNL IT

HTLV-1  YS SY H A TYSLYLFPHW T KKPNR NGG GYYS A SY S DPCSL K CPYLGCQSWTCPYTG A VSSP Y WKF QH DVNFTQE
HTLV-2  YS GF H K TYSLYLFPHW I KKPNR QGL GYYS P SY N DPCSL Q CPYLGCQSWTCPYTG P VSSP S WKF HS DVNFTQE

HTLV-1  VS RLNIN LHFSKCG FPFS LLVDAPGYDP I WF LNT EP S Q L PPT A PPL LPH S N L D HI L E PS IPW KS K L L TLV QL
HTLV-2  VS QVSLR LHFSKCG SSMT LLVDAPGYDP L WF ITS EP T Q P PPT S PPL VHD S D L E H V L T PS TS W TT K I L KFI QL

HTLV-1  TLQSTNY T C I VC I DR A SLS T WHVLY S PN V S V P --SS SS TPL L Y PSLALPAP HLTL P FN WTHC FD P QI QAI VSS
HTLV-2  TLQSTNY S C M VC V DR S SLS S WHVLY T PN I S I P QQT SS RTI L F PSLALPAP PSQ- P SL WTHC YQ P RL QAI TTD
```

FIG. 1-2

```
HTLV-1  PCHNSL ILPPFSL S PVP TL GS R S RRAVP V AWLV S ALA M G A G V AGG IT GS M SLAS G KSLL H EVDKDIS Q LTQ
HTLV-2  NCNNSI ILPPFSL A PVP PL AT R R RRAVP I AWLV P ALA A G T G I AGG VT GS L SLAS S KSLL L EVDKDIS H LTQ

HTLV-1  AIVKNH K N L KI A N YAAQNRRGLDLLFWEQGGLCKA L QEQC R F P NI T N S HV PI LQERPPLE N RV L TGWGLNW
HTLV-2  AIVKNH Q N I L RV A Q YAAQNRRGLDLLFWEQGGLCKA I QEQC C F L NI S N T HV SV LQERPPLE K RV I TGWGLNW

HTLV-1  DLGLSQWAREALQTGIT LV ALLLIVIL A GPCILRQ LRH LP S R V-- R YPH YSLI K PE SS L
HTLV-2  DLGLSQWAREALQTGIT IL ALLLIVIL F GPCILRQ IQA LP Q R LQN R HHQ YSLI N PE TM L
```

FIG. 2A

EPITOPE I:

| Sequence | Virus |
|---|---|
| FSLLVDAPGYDPIWFLNTEPSQLPPTAPPLLPHSNLDHILEPSIPWKSKLLTLVQLTLQS | HTLV-1 |
| MTLLVDAPGYDPLWFITSEPTQPPPTSPPLVHDSDLEHVLTPSTSWTTKILKFIQLTLQS | HTLV-2 |

| Sequence | Peptide No. | Relative Immunoreactivity |
|---|---|---|
| APPLLPHSNLDHILEPSIPWKSKLLTLVQLTLQS | IV | ++++ |
| FSLLVDAPGYDPIWFLMTEPSQLPPTAPPLLPHSN | XII | +/- |
| SPPLVHDSDLEHLVTPSTSWTTKILKFIQLTLQS | X* | ++++# |

* Analogue of IV

FIG. 2B

EPITOPE I:

HVLYSPNVSVPSSSSTPLLYPSLALPAPHLTLPFNWTHCFDPQIQAIVSSPCHNSLILPPFSLSPVPTLGSRSRRA
HVLVTPNISIPQTSSRTILFPSLALPAPPSQ-PSLWTHCYQPRLQAITTDNCNNSIILPPFSLAPVPPLATRRRRA

| Sequence | Peptide No. | HTLV-1 Relative Immunoreactivity | HTLV-2 |
|---|---|---|---|
| HVLYSPNVSVPSSSSTPLLYPSLALPAPHLTL | XIII | +/− | |
| SSTPLLYPSLALPAPHLTLPFNWTHCFDPQIQAIVSSPCH | V | ++++ | +++ |
| LYPSLALPAPHLTLPFNWTHCFDPQIQAIVSSPCH | Ve | ++++ | +++ |
| ALPAPHLTLPFNWTHCFDPQIQAIVSSPCH | Vd | ++++ | +++ |
| HLTLPFNWTHCFDPQIQAIVSSPCH | Vc | ++++ | +++ |
| FNWTHCFDPQIQAIVSSPCH | Vb | ++ | ++ |
| CFDPQIQAIVSSPCH | Va | ++ | ++ |
| CFDPQIQAIVSSPCHNSLILPPFSLSPVPTLGSRSRRA | VI | ++++ | ++++ |
| QIQAIVSSPCHNSLILPPFSLSPVPTLGSRSRRA | VIe | +++ | +++ |
| IVSSPCHNSLILPPFSLSPVPTLGSRSRRA | VId | ++ | ++ |
| HNSLILPPFSLSPVPTLGSRSRRA | VIc | ++ | ++ |
| ILPPFSLSPVPTLGSRSRRA | VIb | + | + |
| SLSPVPTLGSRSRRA | VIa | +/− | +/− |
| ALPAPPSQ-PSLWTHCYQPRLQAITTDNCN | XIa* | +/− | +/− |
| LFPSLALPAPPSQ-PSLWTHCYQPRLQAITTDNCN | XIb | + | + |
| SSRTILFPSLALPAPPSQ-PSLWTHCYQPRLQAITTDNCN | XI | ++ | ++ |

* Analogue of IV

SYNTHETIC PEPTIDE COMPOSITIONS WITH IMMUNOREACTIVITIES TO ANTIBODIES TO HTLV

This Application is a divisional of 07/901,874, filed Jun. 22, 1992, now U.S. Pat. No. 5,476,765, which is a continuation-in-part of Application Ser. No. 07/469,291, filed Jan. 24, 1990, which is continuation-in-part of Application Ser. No. 07/297,635, filed Jan. 13, 1989, now abandoned which is in turn a continuation-in-part application of Application Ser. No. 07/001,885, filed Jan. 9, 1987, which has now issued a U.S. Pat. No. 4,833,071 in May 23, 1989.

Human T-cell leukemia viruses have been linked to certain adult lymphoid malignancies, notably adult T-cell leukemia-lymphoma (ATL) and hairy cell leukemia (HCL) (1–3, 24 and 25). There are two recognized subgroups, HTLV-I and HTLV-II. Up to the present, much of the work is directed to HTLV-I prevalent in ATL patients in Japan. However, recent studies show that the HTLV-II is more prevalent in the intravenous drug users in the metropolitan areas of U.S.A. (27, 28). Antibodies that react with HTLV proteins have been found in sera of ATL patients. These HTLV antibodies recognize both the gag core antigens and the envelope proteins of the viruses (4, 5, 27). Human Immunodeficiency Virus (HIV) is a retrovirus causatively linked to Acquired Immune Deficiency Syndrome (AIDS) and AIDS related complex (ARC). Antibodies that react with HIV proteins have been found in the sera of AIDS and ARC patients. These HIV antibodies recognize both the gag core antigens and envelope proteins of the HIV virus. In the United States, the disease AIDS is far more prevalent than ATL, with some individuals seropositive for HIV also being seropositive for HTLV.

The present invention relates to highly sensitive methods for the detection of antibodies to HTLV-I and/or HTLV-II in body fluids by the use of synthetic peptide compositions. The present invention further relates to a highly sensitive method for the simultaneous detection of antibodies to HTLV-I, HTLV-II and HIV in body fluids by the use of synthetic peptide compositions. One peptide composition comprises peptides having amino acid sequences corresponding to segments of the external (extracellular) portion of the HTLV-I and HTLV-II env protein, designated gp46, and may further comprise peptides having amino acid sequences corresponding to segments of the transmembrane portion of the HTLV-I/HTLV-II env protein, designated gp21. These sequences have been found to be highly immunoreactive to antibodies in the sera of patients with ATL and HTL. Such peptide compositions are also useful for the production of a vaccine to prevent ATL or HTLV-II infection by stimulating the production of antibodies to HTLV-I/HTLV-II, which provide protection against HTLV-I/HTLV-II infection in healthy mammals, including humans. Furthermore, a peptide composition comprising peptides with amino acid sequences corresponding to portions of HTLV-I/HTLV-II envelope proteins may be used in conjunction with a peptide composition comprising peptides with amino acid sequences corresponding to portions of the MIr envelope and core proteins for the simultaneous detection of antibodies to HTLV-I, HTLV-II and HIV.

More specifically, the present invention is directed to peptide compositions, useful for the detection of HTLV-I and/or HTLV-II antibodies, which comprise peptides selected from the group consisting of chemically synthesized peptides containing about thirty-four, forty, thirty-eight, twenty, twenty-four and sixteen amino acids, or their analogues, in a prescribed sequence; analogues, segments, mixtures, conjugates and polymers thereof. The invention is further directed to the use of an HTLV-I and/or HTLV-II peptide composition in conjunction with an HIV peptide composition which comprises peptides selected from the group consisting of chemically synthesized peptides containing about twenty-one, nineteen, eleven and sixteen amino acids, sequence; analogues, segments, mixtures, conjugates and polymers thereof, for the simultaneous detection of antibodies to HTLV-I, HTLV-II and HIV in human body fluids. The present invention also provides a method for diagnosing HTLV infection, HTLV-I or HTLV-II infection.

The detection methods include an enzyme-linked immunoadsorbent assay (ELISA), multi-dot, multi-line, or multi-square blotting on nitrocellulose paper, and a passive hemagglutination assay using the peptides as the solid phase antigens. The preferred detection method is by ELISA.

Another objective is to develop an immunogen or a vaccine which, when introduced into healthy mammals, including humans, will stimulate one production of efficacious antibodies to HHTL.

BACKGROUND OF THE INVENTION

The human T cell leukemia-lymphoma viruses (HTLV) are a family of =elated retroviruses originally isolated from patients with T cell lymphoma and cutaneous manifestations. A particular subgroup of the family, type I, now known as HTLV-I, has been causatively linked to malignancies which share clinical and epidemiologic features with the disease called adult T-cell leukemia-lymphoma (ATL) which occur in certain regions of Japan (6-9), the Caribbean Basin (10,11) and the southwestern United States (12). There are no known enaemic areas for HTLV-II and no known casual relationship between any specific disease with HTLV-II. The source of HTLV-II virus introduced into the intravenous drug users is not known. Widescale seroprevalence studies for HTLV-II have not been carried out.

HTLV-II is structurally very similar to HTLV-I. The two viruses share approximately 50% sequence homology (29). HTLV-II was isolated from one patient who had hairy cell leukemia but no casual relationship was found. The amino acid sequence of the env protein of HTLV-II is identical to that of HTLV-I for 69% of the residues, and an additional 14% of the amino acids represent conservative substitutions (30, 31). The X and pol genes are even more highly conserved than the env gene (32).

Because of the high degree of homology between HTLV-I and HTLV-II, standard testing assays by ELISA for HTLV-I based on whole viral lysate or recombinant proteins also cross react with HTLV-II. The peptides disclosed in U.S. Pat. No. 4,833,071 are also cross reactive with HTLV-II. No effective serological assay exists to distinguish between HTLV-I and HTLV-II env proteins although antigenic differences between the two viruses have been detected by neutralization of vesicular stomatitis virus pseudotypes (5). Two supplemental methods have been employed to confirm that antibodies to HTLV are present in samples that are shown to be reactive in am HTLV-I enzyme immunoassay. The Western Blot method for HTLV-I gives bands at p15, p19, p24, p28, p32, p36 and p55 for core proteins and at gp45 and gp61 for envelope proteins (32). The radioimmuno precipitation assay (RIPA) for HTLV-I gives bands for gp45 and gp61 for env proteins, p24 and p55 for core, and p40x for the X region (31). Neither tests, however, distinguish between the two viruses.

PCR has recently been used to distinguish between HTLV-I and HTLV-II. The PCR method provides definitive results (28). However, because of its exquisite sensitivity, it is subject to false positive results. Moreover, it is a very time consuming and expensive test.

Although the mechanism of transmission of HTLV-I is currently unknown, horizontal transmission of HTLV is clearly implicated by molecular and epidemiologic analyses (13,14). HTLV seropositivity in regions endemic for ATL is elevated overall in the general population and further elevated among close family members of patients and in the recipients of blood transfusions (15,16). HTLV-II seropositivity has been identified in intravenous drug users in the metropolitan areas of U.S.A. (27, 28).

This means that there is an urgent need for a safe, reliable and sensitive test to screen each blood sample before its inclusion in blood banks and to isolate blood donations derived from HTLV-I and/or HTLV-II infected individuals to avoid the inadvertent spread of the virus among patients who must receive blood transfusions, e.g. hemophiliacs and surgical patients.

There is an urgent need for a rapid and less expensive method to distinguish between infection with HTLV-I and HTLV-II. Since 1988, mandatory screening of all donors for HTLV-I has been performed and donors reactive for HTLV-I, as well as HIV must be notified of their results. The uncertainty as to which virus, HTLV-I or HTLV-II, is responsible for seropositivity, renders it very difficult to counsel the donors accurately about their risk for contracting ATL or a neurological complication of HTLV-I. A method for distinguishing HTLV-I from HTLV-II is also important for seroprevalence studies to define endemic areas for HTLV-II and pathogenicity studies for both viruses (33).

The complete nucleotide sequence of the HTLV-I virus was reported in 1983 (17). This report elucidated the structure of the HTLV-I virus at both the DNA level and the predicted protein level and permitted further serological studies of the different epitopes which may be present on the HTLV-I virus. The nucleotide sequence of the HTLV-II virus was reported in 1984, 1985 and 1986 (30, 31, 32).

Simultaneous to Seiki et al's report in 1983, Dr. Carl Saxinger at National Cancer Institute reported that the use of the isolated HTLV-I virus as a solid-phase immunoadsorbent for the development of an enzyme immunoassay for the detection of HTLV-I antibodies in the African population (18).

It was further reported by Samuel et al. (19) that a combined cloning and expression system in *E. coli* has been used to identify HTLV-I DNA encoded glycoproteins which reacted immunologically with antibodies in sera from ATL patients. HTLV-I DNA encoding the envelope protein was cleaved into fragments and inserted into an expression vector. The expression vectors were introduced into an *E. coli* host by transformation. One clone, designated as pKS400, produced an envelope protein product found to be suitable for use as an immunoadsorbent to screen a group of 28 coded sera. Antibodies that recognized the bacterially synthesized HTLV-I envelope protein sequences were found in all sera that had been shown to have antibodies to HTLV by an ELISA assay with disrupted virions as the antigen (18).

Slamon et al, Application No. PCT/US 85/01803, published on Mar. 27, 1986 under Publication No. WO86/01834, described polypeptides associated with immunogenic sites of HTLV-I as expression products of the X region of HTLV-I, a highly conserved region location between env and the 3 LTR of the virus. The proteins, with a molecular weight of between 37 kd and 40 kd, were cloned and expressed as fusion proteins in *E. coli*. The resulting products were purified and used in liquid phase immunoprecipitation tests to screen sera. The results indicated an accuracy of from about 77% to 87% (20). All of the above failed to distinguish between infection by HTLV-I or HTLV-II because of the antigens used to detect the immunoreactivity.

Synthetic peptides have been used increasingly to map antigenic or immunogenic sites on the surface of proteins and as possible vaccines. The named inventor and a colleague previously have taken this approach to identify and characterize highly antigenic epitopes on the envelope proteins of HTLV and to develop sensitive and specific immunoassays for the detection of antibodies to HIV (previously designated HTLV-III) (21). See also U.S. Pat. No. 4,735,896, issued Apr. 5, 1988 and U.S. Pat. No. 4,879,212 issued Nov. 7, 1989, the contents of which are, hereby, fully incorporated by reference (22, 23). A similar approach is employed in this invention to select and identify highly antigenic epitopes in HTLV-I and HTLV-II. In selecting regions of the envelope protein for epitope analysis, several strategies were employed. First, regions that exhibited a relatively high conservation of amino acid sequence between HTLV-I and HTLV-II were sought. Second, multiple overlapping linear peptides covering whole regions of gp21, the transmembrane portion of the HTLV envelope protein (See FIG. 1), were synthesized and characterized. Third, multiple overlapping linear peptides covering the whole region of gp46, the external portion of the HTLV envelope protein (See FIG. 1), were synthesized and characterized. Three peptides, from the transmembrane portion, with the following sequences (See FIG. 2), and a mixture thereof, were found to be highly immunoreactive with sera from patients with ATL:

GLDLLFWEQGGLCKALQEQC-NH2 SEQ ID NO: 1 (I)

QNRRGLDLLFWEQGGLCKALQEQC-NH2 SEQ ID NO: 2 (II)

NRRGLDLLFWEQGGLC-NH2 SEQ ID NO: 3 (III)

and three peptides, from the external portion, with the following sequences, and a mixture thereof, were also found to be highly immunoreactive with sera from patients with ATL (See FIG. 3):

APPLLPHSNLDHILEPSIPWKSKLLTLVQLTLQS-NH$_2$ SEQ ID NO: 4 (IV)

SSTPLLYPSLALPAPHLTLPFNWTHCFDPQIQAIVSSPCH-NH$_2$ SEQ ID NO: 5 (V)

CFDPQIQAIVSSPCHNSLILPPFSLSPVPTLGSRSRRA-NH$_2$ SEQ ID NO: 6 (VI)

wherein:

| | |
|---|---|
| A = Ala = alanine, | G = Gly = glycine, |
| R = Arg = arginine, | I = Ile = isoleucine, |
| D = Asp = aspartic acid, | F = Phe = phenylalnine, |
| N = Asn = asparagine, | S = Ser = serine, |
| Q = Gln = glutamine, | W = Trp = tryptophan |
| E = Glu = glutamic acid, | Y = Tyr = tyrosine, |
| L = Leu = leucine, | V = Val = valine, |
| K = Lys = lysine, | C = Cys = cysteine, |
| H = His = histidine, | P = Pro = proline |
| T = Thr = threonine | |

An example of an analogue peptide corresponding to Peptide IV of HTLV-I and found in the same region of HTLV-II contains the following sequence:

SPPLVHDSDLEHVLTPSTSWTTKILKFIQLTLQS-NH$_2$ SEQ ID

NO: 10 (X)

Peptides I, II and III were described in the parent application which has now issued as U.S. Pat. No. 4,833,071.

Assays for antibodies to HTLV-I and/or HTLV-II based upon chemically synthesized peptides show several advantages over assays utilizing whole disrupted virus or bacterially produced immunoadsorbents. The peptides can easily be synthesized in gram quantities by using automated solid-phase methods, thus providing a reproducible antigen of high integrity with consistent yields. Isolation of antigens from biological systems precludes such reproducibility. More importantly, non-specific reactivities seen in non-HTLV-I or non-HTLV-II infected individuals are likely due to the heterogeneity of the preparations used for assay. This is particularly true for assays using either whole virus or *Escherichia coli*-derived recombinant products as immunoadsorbents. In these processes, the major histocompatibility antigens or endogenous bacterial proteins of the host cells are frequently copurified with the desired antigen virus or protein. Since antibodies to these contaminating antigens are frequently found in normal individuals, false-positive results cannot be eliminated by using current antigen isolation processes.

The assay of the present invention thus clearly eliminates those false-positive reactions encountered in the other methods and, at the same time, shows a high sensitivity to truly positive sera by the substantially increased signal-to-noise ratio. This increased signal-to-noise ratio likely results from the purity of the immunoadsorbent. The assay of the present invention is also highly specific, in that peptide IV and its HTLV-II analogue (peptide X) are also found to be useful to distinguish between individual sera infected with HTLV-I or HTLV-II. That is to say, peptide IV preferentially detects antibodies to HTLV-I but not HTLV-II, and vice versa.

Furthermore, up to the present, no viable vaccine or method to provide protection against HTLV-I or HTLV-II infection has been reported. Utilization of deactivated virus provokes fears of contracting the disease, preventing its acceptability and use.

It is, therefore, an objective of the present invention to develop a detection or diagnostic procedure that does not require the use of the virus or lysates thereof as a test reagent.

A further objective is to develop a test procedure that is highly sensitive and accurate.

A further objective is to prepare a test reagent by chemical means. The synthetic reagent can than be used to detect the presence of antibodies to HTLV-I and/or HTLV-II in body fluids and diagnose ATL, thereby avoiding the danger of exposure to the virus or segments thereof and the unnecessary proliferation of the virus.

It is also an objective of the present invention to have a test reagent and procedure which can distinguish between HTLV-I and HTLV-II infection, to enable the medical profession to study the etiology of HTLV-II infection, the diseases caused by the HTLV-II virus, and its effect on the development of HIV infection in patients who are infected with both HIV and HTLV-II.

Another objective is to develop a vaccine which, when introduced into healthy mammals, including humans, will stimulate production of antibodies to HTLV-I, thereby providing protection against HTLV-I infection.

A further objective is to provide a non-viral immunogen which can be used in mammals for the development of monoclonal and polyclonal antibodies to HTLV-I.

REFERENCES

1. B. J. Poiesz., et al., *Proc. Natl Acad. Sci. USA.*, 77:7415 (1980).
2. B. J. Poiesz., F. W. Ruscetti, M., S. Reitz., V. S. Kalyanaraman, R. Gallo *Nature* (London) 294:268 (1981).
3. R. C. Gallo et al., *Proc, Natl Acad. Sci. USA.*, 79:5680 (1982).
4. M. Essex et al., *Science* 221:1061 (1983).
5. P. Clapman, K. Napy, R. A. Weiss, *Proc. Natl. Acad. Sci.* 81:2886 (1984).
6. R. C. Gallo et al., *Cancer Res.*, 43:3892 (1983).
7. R. C. Gallo, *Cancer Surveys*, L. M. Franks et al. Eds, (University Press, Oxford, in press)
8. W. A. Blattner, K. Tokatsuki, R. C. Gallo, *J. Am. Med. Assoc.*, 250:1074 (1983).
9. K. Takatsuki, J. Uchiyama, K. Sagawa, J. Yodoi, *Topics in Hematology*, S. Seno, F. Takaku, S. Irino, Eds. (Excerpts Medica, Amsterdam, 1977) p73.
10. W. A. Blattner et al., *Int. J. Cancer*, 30:257 (1982).
11. D. Catovsky et al., *Lancet*, 1982-I, 639 (1982).
12. D. W. Blayney et al., *J. Am. Med. Assoc.*, 250:1048 (1983).
13. M. Robert-Guroff, F. W. Ruscetti, L. W. Posner, B. J. Poiesz, R. C. Gallo, *J. Exp. Med.*, 154:1957 (1981).
14. R. C. Gallo et al., *Proc. Natl. Acad. Sci., USA*, 79:5680 (1981).
15. M. Robert-Guroff et al., *J. Exp. Med.*, 157:248 (1983).
16. M. Shimoyama et al, *Jpn. J. Clin. Oncol.*, 12:109 (1982).
17. M. Seiki, S. Hattori, Y. Hirayama, M. Yoshida, *Proc. Natl Acad. Sci. USA*, 80:3618 (1983).
18. Saxinger, C. W. et al., *Science*, 225:1473 (1984).
19. Samuel, K. P. et al., *Science*, 226, 1094–1097 (Nov. 30, 1984).
20. Slamon et al., PCT Pat. No. Publication No. WO86.01834.
21. Wang, J. J-G, Steel, S., Wisniewolski, R. and Wang, C. Y. *Proc. Natl. Acad. Sci. USA*, 83, pp 6159–6163 (August 1986).
22. U.S. Pat. No. 4,735,896, issued Apr. 5, 1988 to Chang Y. Wang and James G. Wang.
23. U.S. Pat. No. 4,879,212 issued Nov. 7, 1989 to Chang Y. Wang and James G. Wang.
24. Liu, Fu-Tong et al., *Biochemistry*, 18, pp. 690–697 (1979).
25. V. S. Kalyanaraman, M. G. Sarnagadharan, M. Robert-Guroff et al., Science, 218, 571 (1982).
26. J. D. Rosenblatt et al., *N. Engl. J. Med.*, 315:372 (1986).
27. M. Robert-Guroff, S. H. Weiss, J. H. Giron et al., *J. Am Med. Assoc.*, 255:3133 (1986).
28. H. Lee, P. Swanson, V. S. Shorty et al., *Science*, 244:471 (1989).
29. R. C. Gallo, *Med. Oncol. Tumor Pharmacother.*, 3:265 (1986).
30. K. Shimotolino, Y. Takahashi, et al., *PNAS USA*, 82, 3101–3105 (May 1985). J. Sodroski, R. Patarca, D. Perkins et al., *Science*, 225:421 (1984).
32. G. M. Shaw, M. A. Gonda, G. H. Flickinger et al., *PNAS USA*, 81:4544 (1984).
33. S. G. Sandlet, C. Fang, in *Transfusion-Transmitted Vital Disease*, Arlington, VA:American Assn. of Blood Bankers, p. 19 (1987).

BRIEF DESCRIPTION OF THE INVENTION

According to the present invention, four additional peptides, each arranged in a specific sequence, have been made by solid phase peptide synthesis. These peptides have been found to be useful in a highly sensitive and accurate method for the detection of antibodies to HTLV-I/HTLV-II in sera and body fluids and in the diagnosis of ATL. Because of the high immunoreactivity, it is expected that the peptides are also useful in stimulating production of antibodies to HTLV-I/HTLV-II in healthy mammals such as Balb/c mice.

According to the present invention, a peptide composition useful for the detection of antibodies to HTLV-I/HTLV-II and diagnosis of ATL comprises a peptide selected from the group of peptides comprising:

APPLLPHSNLDHILEPSIPWKSKLLTLVQLTLQS-X SEQ ID NO: 4 (IV)

SSTPLLYPSLALPAPHLTLPFNWTHCFDPQIQAIVSSPCH-X (SEQ ID NO: 5 (V)

CFDPQIQAIVSSPCHNSLILPPFSLSPVPTLGSRSRRA-X SEQ ID NO: 6 (VI)

SPPLVHDSDLEHVLTPSTSWTTKILFIQLTLQS-X SEQ ID NO: 10 (X)

wherein X is —OH or —NH$_2$, analogues, segments, mixtures conjugates and polymers thereof, wherein:

| | |
|---|---|
| A = Ala = alanine, | G = Gly = glycine, |
| R = Arg = arginine, | I = Ile = isoleucine, |
| D = Asp = aspartic acid, | F = Phe = phenylalanine, |
| N = Asn = asparginine, | S = Ser = serine, |
| Q = Gln = Glutamine, | W = Trp = tryptophan, |
| E = Glu = Glutamic acid, | Y = Tyr = tyrosine, |
| L = Leu = Leucine, | V = Val = valine, |
| K = Lys = Lysine, | C = Cys = cysteine, |
| H = His = histidine | P = Pro = proline |
| T = Thr = threonine | |

The highly sensitive and accurate method of detecting antibodies to HTLV-I/HTLV-II in body fluids and diagnosis of ATL comprises the following steps:

A. Preparing peptides composition comprising a peptide selected from the group having the following amino acid sequences:

APPLLPHSNLDHILEPSIPKWKSKLLTLVQLTLQS-X SEQ ID NO: 4 (IV)

SSTPLLYPSLALPAPHLTLPFNWTHCFDPQIQAIVSSPCH-X SEQ ID NO: 5 (V)

CFDPQIQAIVSSPCHNSLILPPFSLSPVPTLGSRSRRA-X SEQ ID NO: 6 (VI)

SPPLVHDSDLEHVLTPSTSWTTKILKFIQLTLQS-X SEQ ID NO: 10 (X)

wherein X is —OH or NH$_2$, analogues, segments, mixtures, conjugates and polymers thereof; and B. Using about 0.01 ug to about 20 ug per test in a buffer at a pH of about 7 to 10, of the peptide composition as the antigen in an immunoassay procedure.

Further, according to the present invention, the peptides by themselves, or when coupled to a protein or a polymer carrier, or when polymerized to homo or hetero dimers or higher oligomers by cystsine oxidation, induced disulfide cross linking reagents, or when directly synthesized onto a polyvalent lysine resin, can be used to stimulate production of antibodies to HTLV-I and/or HTLV-II in healthy mammals, including humans. The method comprises introducing an effective amount of the peptide composition including a mixture of these six peptides, conjugated to a carrier, such as human serum albumin, or as a polymer, into the body of a healthy mammal by intraperitoneal or subcutaneous injection.

Analoguss of peptides I to VI can be found in HTLV-II See FIG. 1. Such sequences are:

GLDLLFWEQGGLCKAIQEQC-X SEQ ID NO: 7 (VII)

QNRRGLDLLFWEQGGLCKAIQEQC-X SEQ ID NO: 8 (VIII)

NRRGLDLLFWEQGGLC-X SEQ ID NO: 9 (IX)

SPPLVHDSDLEHVLTPSTSWTTKILKFIQLTLQS-X SEQ ID NO: 10 (X)

SSRTILFPSLALPAPPSOPSLWTHCYOPRLQAITTDNCN-X SEQ ID NO: 11 (XI)

CYQPRLQAITTDNCNNSIILPPFSLAPVPLATRRRRA-X SEQ ID NO: 12 (XII)

(The differences from HTLV-I have been underscored.)

Peptides VII to XII are useful for detecting antibodies to HTLV-II in body fluids. A review of these sequences show that peptide IX is identical to peptide III; peptides VII and VIII are identical to peptides I and II except for one amino acid; whereas peptides X, XI and XII contain multiple sites where the amino acids are substituted according to the corresponding HTLV-II amino acids sequence and are, therefore, quite different from that in peptides IV, V and VI.

It has been found that peptide IV and X are specific for HTLV-I and HTLV-II respectively. That is, peptide IV is not s reactive to antibodies to HTLV-II and peptide X is not as reactive to antibodies to HTLV-I. Because of this, peptides IV and X may be used to distinguish between HTLV-I and HTLV-II seropositivity.

In addition, according to the present invention, mixtures of peptides IV-XII may be used to detect the presence of HTLV-I/II in body fluids. Further, a peptide composition useful for the detection of antibodies to HTLV-I/HTLV-II may be used in conjunction with peptide compositions useful for the detection of antibodies to HIV-1 and HIV-2, for the simultaneous detection of infection by both HTLV-I and II and HIV-1 an HIV-2. Peptide compositions useful for the detection of antibodies to HIR-1 and HIV-2 comprise chemically synthesized peptides of the following amino acids, or their analogues, in the prescribed sequences wherein the sequence for HIV-2 is an analogue of peptide VII and peptide VIII:

HIV-1

RILAVERYLKDQQLLGIWGCS-X SEQ ID NO: 13 (XIII)

IWGCSGKLICTTAVPWNAS-X SEQ ID NO: 14 (XIV)

IVRMYSPTSIL-X SEQ ID NO: 15 (XV)

HIV-2

DQARLNSWGCAFRQVC SEQ ID NO: 16 (XVI)

wherein X is —OH or —NH$_2$, and include analogues, segments, mixtures and polymers thereof, wherein:

| | |
|---|---|
| A = Ala = alanine, | G = Gly = glycine, |
| R = Arg = arginine, | I = Ile = isoleucine, |
| D = Asp = aspartic acid, | F = Phe = phenylalanine, |
| N = Asn = asparginine, | S = Ser = serine, |
| Q = Gln = Glutamine, | W = Trp = tryptophan, |
| E = Glu = Glutamic acid, | Y = Tyr = tyrosine, |
| L = Leu = Leucine, | V = Val = valine, |
| K = Lys = Lysine, | C = Cys = cysteine, |
| H = His = histidine | P = Pro = proline |
| T = Thr = threonine | |
| M = Met = methionine | |

The underlined amino acids indicate the residues shared between various isolates. For HIV-2 peptide XVI, substitutions were made in the corresponding HIV-2 envelope protein amino acid sequence that would be predicted from the nucleotide sequence.

BRIEF DESCRIPTION OF THE DRAWING

FIG. 1 shows and compares the amino acid sequences of the HTLV-I and HTLV-II envelope proteins.

FIG. 2 shows the amino acid sequences of the chemically synthesized peptides described herein.

FIG. 3 is a histogram depicting the immunoreactivities described herein, with sera from ATL patients.

DETAILED DESCRIPTION OF THE INVENTION

Figure 4:
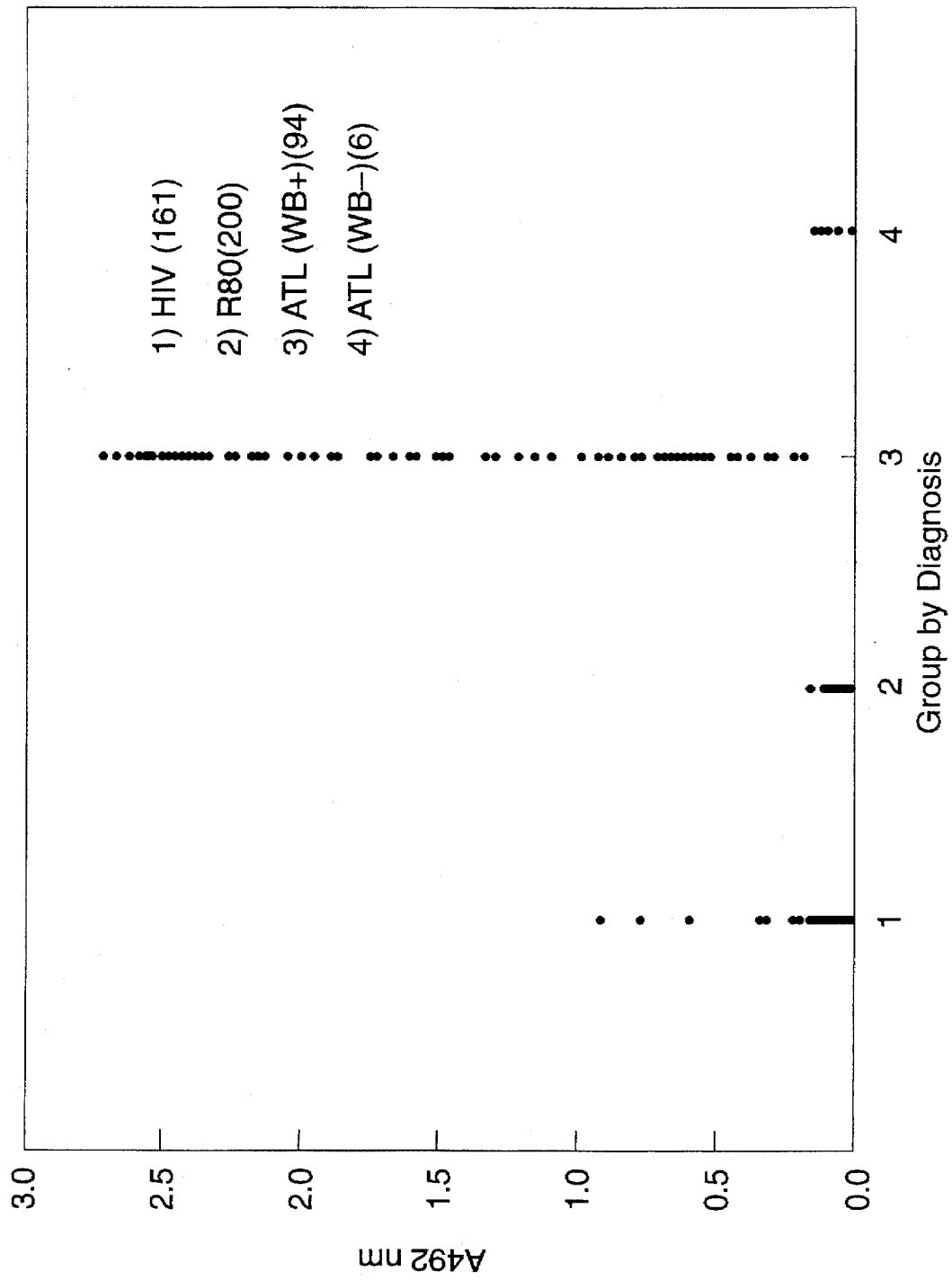
FIG. 4 is a histogram depicting the immunoreactivities of the peptides described herein with sera from patients with HIV infection, patients with ATL, and random blood donors.

In accordance with the present invention, six peptides have been chemically synthesized for the detection of antibodies to HTLV-I or HTLV-II in body fluids and the diagnosis of ATL, and for the vaccination of healthy mammals by stimulating the production of antibodies to HTLV-I or HTLV-II in healthy mammals. These peptides are arranged in the following sequences:

GLDLLFWEQGGLCKALQEQC-X SEQ ID NO: 1 (I)

QNRRGLDLLFQEQGGLCKALQEQC-X SEQ ID NO: 2 (II)

NRRGLDLLFWEQGGLC-X SEQ ID NO: 3 (III)

APPLLPHSNLDHILEPSIPWKSKLLTLVQLTLQS-X SEQ ID NO: 4 (IV)

SSTPLLYPSLALPAPHLTLPFNWTHCFDPQIQAIVSSPCH-X SEQ ID NO: 5 (V)

CFDPQIQAIVSSPCHNSLILPPFSLSPVPTLGSRSRRA-X SEQ ID NO: 6 (VI)

SPPLVHDSDLEHVLTPSTSWTTKILKFIQLTLQS-X SEQ ID NO: 10 (X)

wherein X is —OH or —NH$_2$.

These peptides may also comprise conjugates, i.e., they may be coupled to carrier proteins such as bovine serum albumin (BSA) or human serum albumin (HSA). Furthermore, these peptides may comprise polymers, i.e., they may be synthesized on a polymeric resin, such as a branching octameric lysine resin. It is expected that as long as the peptide immunoreactivities recognizable by the antibodies to HTLV-I/HTLV-II are preserved, analogues of the synthetic peptide may also comprise substitutions, insertions and/or deletions of the recited amino acids of the above sequence.

In addition, to accommodate strain-to-strain variations among different isolates, adjustments for conservative substitutions and selection among the alternatives where non-conservative substitutions are involved, may be made in the prescribed sequences. For example, peptides X to XII found in the HTLV-II strain may also be used.

The amino acid sequences of the polypeptides useful as test reagents for the detection of antibodies to HTLV-I or HTLV-II in body fluids and diagnosis of ATL are selected to correspond to a partial segment of the amino acid sequence of the HTLV-I virus designated as gp21, and to a partial segment of the amino acid sequence of the HTLV virus designated as gp46, both parts of gp61, which defines the envelope protein of the HTLV-I or HTLV-II virus.

The peptides useful as solid phase immunoadsorbents for the detection of antibodies HTLV-I were synthesized by the "classical" Merrifield method of solid phase peptide synthesis using side chain protected t-Boc-amino acids to correspond to the following amino acid sequences:

APPLLPHSNLDHILEPSIPWKSKLLTLVQLTLQS-X SEQ ID NO: 4 (IV)

SSTPLLYPSLALPAPHLTLPFNWTHCFDPQIQAIVSSPCH-X SEQ ID NO: 5 (V)

CFDPQIQAIVSSPCHNSLILPPFSLSPVPTLGSRSRRA-X SEQ ID NO: 6 (VI)

SPPLVHDSDLEHVLTPSTSWTTILKFIQLTLQS-X SEQ ID NO: 10 (X)

wherein X is —OH or —NH$_2$.

Other analoguss of these peptides can be prepared by varying the amino acid sequences either by adding, subtracting, substituting, or deleting desired t-Boc-amino acid(s).

For example, analogue peptides VII to XII having following sequences can also be prepared.

GLDLLFWEQGGLCKAIQEQC-X SEQ ID NO: 7 (VII)

QNRRGLDLLFWEQGGLCKAIQEQC-X SEQ ID NO: 8 (VIII)

NRRGLDLLFWEQGGLC-X SEQ ID NO: 9 (IX)

SPPL<u>VHDSDLEHVLTPSTSWTTKIL</u>KFIQLTLQS-X SEQ ID NO: 10 (X)

SS<u>KTIL</u>FPSL<u>ALPAPPSQPSL</u>WTHC<u>YQPRL</u>QA<u>ITTDNCN</u>-X SEQ ID NO: 11 (XI)

C<u>YQPRL</u>QA<u>ITTDNCNNSIIL</u>PPFSL<u>AP</u>VPL<u>ATRRRA</u>-X SEQ ID NO: 12 (XII)

Following completion of assembly of the desired blocked peptide on the resin, the peptide-resin is treated with anhydrous hydrofluoric acid to cleave the peptide from the resin. Functional groups of amino acids which are blocked during synthesis by benzyl-derived blocking groups are also cleaved from the peptide simultaneously. The free peptide is then analyzed and purified by high performance liquid chromatography (HPLC) and characterized biochemically by amino acid analysis.

The peptides synthesized according to the above described procedure are highly reactive to antibodies to HTLV-I and/or HTLV-II and can be used as a highly sensitive and specific immunoadsorbent for the detection of the antibodies against HTLV-I and/or HTLV-II.

Figure 3:
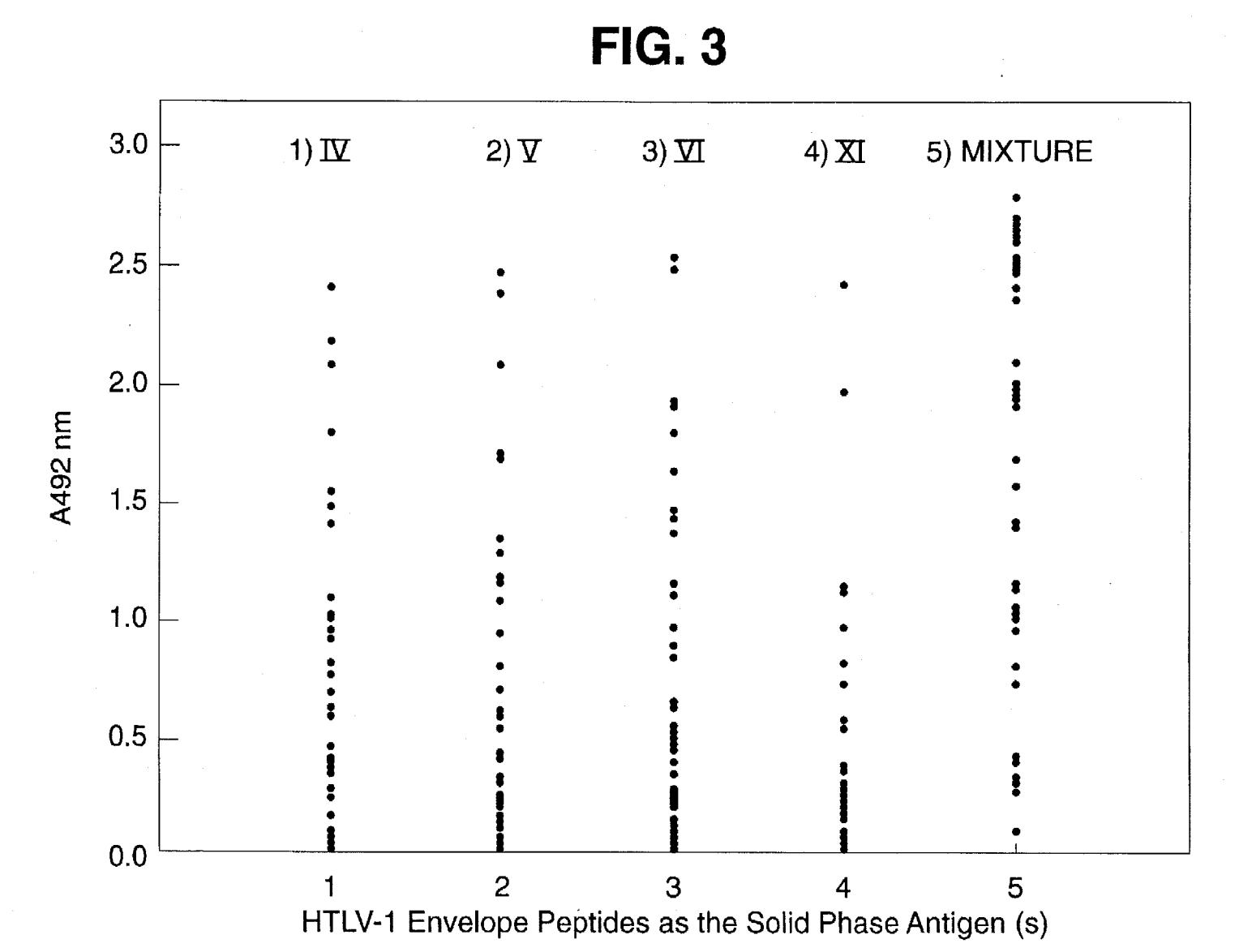

FIG. 3 show the data obtained with sera from ATL patients using an ELISA method wherein the well plates are coated with peptides IV, V and VI at 1.0 ug of each. Table I shows the data obtained with sera from ATL patients using an ELISA method wherein the well plates are coated with a mixture of peptides II, IV, v and VI, in a weight ratio of 1:0.25:1:1 (II;IV;V;VI). Table II shows the data obtained with sera from ATL patients utilizing an agglutination method wherein the red blood cells (RBC) are coated with a peptide VI-BSA conjugate. Tables III and IV show the unique and specific immuno reactivities associated with peptide IV and peptide X and their usefulness in differentiating between subjects with HTLV-I or HTLV-II infections.

Based on the high degree of sensitivity and specificity of the peptide compositions according to the present invention in the immunoreaction to antibodies to HTLV-I and/or HTLV-II, it is believed that these peptide compositions may also be useful as a vaccine for ATL, and/or HTLV-II infection, and as immunogens for the development of both monoclonal and polyclonal antibodies to HTLV-I and/or HTLV-II in mammals, including humans. The peptide compositions when coupled to a protein or synthesized on a polymer carrier resin (e.g., an octameric lysine resin) or when polymerized to homo or hetero dimers or higher oligomers by cystsine oxidation, induced disulfide cross linking, or when polymerized to homo or hetero dimers or higher oligomers by use of homo or hereto functional multivalent cross linking reagents, can be introduced to normal subjects to stimulate production of antibodies to HTLV-I and/or HTLV-II, and provide protection against infection by HTLV-I and/or HTLV-II in healthy mammals. Since the peptide composition according to the present invention is not derived biochemically from the virus, there is no danger of exposing the normal subjects who are to be vaccinated to the disease.

The advantages of using the peptides according to the present invention are many.

The peptides are chemically synthesized. This means that there is no involvement with the HTLV-I or HTLV-II virus at any time during the process of making the test reagent or the vaccine. During the preparation of the vaccine or the vaccination process, production workers or individuals in the health professions do not risk exposure to the HTLV-I or HTLV-II virus. Further, up to the final step of the test to detect antibodies to HTLV-I or HTLV-II, where the test reagent is exposed to samples of sera or body fluid, there is no risk of exposure of the laboratory worker to the HTLV-I or HTLV-II virus.

Another problem which is avoided by the process of the present invention is the possibility of false positive results caused by the presence of antigenic materials from host cells purified with the HTLV-I or HTLV-II viral lysate preparation or *E-Coli* derived proteins co-purified with expressed viral fragments. Certain normal individuals have antibodies to *E. Coli* or human leukocyte antigens, e.g. HLA, which are cross reactive with the antigenic materials from host cells. Sera samples from these normal individuals may show a positive response in the ELISA or IRMA tests.

Further, with appropriate amino acid analogue substitutions, it is expected that various peptide analogues based on the prescribed amino acid sequence can be synthesized with properties giving rise to lower background readings or better adsorption capacity to solid phases useful for HTLV-I or HTLV-II antibodies screening assays.

Moreover, because the peptide compositions of the present invention are synthetically prepared, the quality can be controlled and as a result, reproducibility of the test results can be assured. Also, since very small amounts of peptides are required for each test procedure, and because the expense of preparing the peptides is relatively low, the cost of screening body fluids for antibodies to HTLV-I or HTLV-II, and diagnosis of ATL and/or HTLV-II infection and the preparation of a vaccine is relatively low.

The peptides prepared in accordance with the present invention can be used to detect HTLV-I and/or HTLV-II infection and diagnosis ATL by using it as the test reagent in an enzyme-linked immunoadsorbent assay (ELISA), an enzyme immunodot assay, an agglutination assay, a radio-immunoradiometric assay (IRMA), or other well-known immunoassays. The preferred method is ELISA. The ELISA technique is exemplified in Examples 1 and 2, the IRMA technique is exemplified in Example 5, and the agglutination assay in Examples 3 and 6.

It is to be noted that in the following methods, 0.25% by weight of glutaraldehyde may be added in the coating buffer to facilitate better peptide binding onto the blades or beads. Further, horseradish peroxidase conjugated mouse monoclonal anti-human IgG antibody may be used in place of horseradish peroxidase conjugated goat anti-human IgG as the second antibody tracer.

The gelatin used in these processes can include calf skin gelatin, pig skin gelatin, fish gelatin or any known available gelatin proteins or be replaced with albumin proteins.

In Example 10, it is shown that peptide IV is preferentially reactive to antibodies to HTLV-I and not reactive to HTLV-II and thus can be used to distinguish HTLV-I infection from HTLV-II infection.

Similarly, in Example 11, it is shown that peptide X, which is an analogue peptide derived from the amino acid sequence of HTLV-II, a variant of HTLV-I, is only reactive to antibodies to HTLV-II and can be used to specifically detect HTLV-II infection.

EXAMPLE I

Detection of Antibodies to HTLV-I/HTLV-II by an Enzyme-Linked Immunoadsorbent Assay Wells of 96-well plates were each coated at 4° C. overnight (or 3 hours at room temperature), with each of the three peptides IV, V, VI prepared as described at 1.0 ug each per well per peptide in 100 ul 10 mM $NaHCO_3$ buffer, pH 9.5. The wells were washed three times with phosphate buffered saline (PBS) and then incubated with 250 ul of 3% by weight of gelatin in PBS at 37° C. for I hour to block non-specific protein binding sites, followed by three more washes with PBS containing 0.05% by volume of Tween 20. The test sera (blood taken from a patient or normal individual) were diluted with PBS containing 20% by volume normal goat serum, 1% by weight gelatin and 0.05% by volume Tween 20 at dilutions of 1:20 volume to volume, respectively. 200 ul of the diluted sera were added of each well and allowed to react for 1 hours at 37° C. The wells were then washed three times with 0.05% by volume Tween 20 in PBS in order to remove unbound Horseradish peroxidase conjugated goat anti-human IgG was used as a second antibody tracer to bind with the HTLV-I antibody-antigen complex formed in positive wells. 100 ul of peroxidase labeled goat anti-human IgG at a dilution of 1:3000 in 1% by volume normal goat serum, 0.05% by volume Tween 20 in PBS was added to each well and incubated at 37° C. for another 15 minutes.

The wells were washed five times with 0.05% by volume Tween 20 in PBS to remove unbound antibody and reacted with 100 ul of the substrate mixture containing 0.04% by weight orthophenylenediamine (OPD) and 0.012% by volume hydrogen peroxide in sodium citrate buffer, pH 5.0. This substrate mixture was used to detect the peroxidase label by forming a colored product. Reactions were stopped by the addition of 100 ul of 1.0M $H_2SO_4$ and the absorbance measured using an ELISA reader at 492 nm (i.e. $A_{492}$). Assays were performed in duplicate with one dilution (1:20) of serum samples from normal individuals or from patients with diseases unrelated to HTLV-I infection used as negative controls. Absorbance readings greater than the cutoff value of $A_{492}=0.12$, (about 3× the mean $A_{492}$ value of normal serum control), were taken as positive. The results are shown in FIG. 3.

EXAMPLE 2

Detection of Antibodies to HTLV by an Enzyme-Linked Immunoadsorbent Assay

Wells of 96-well plates were coated at 4° C. overnight (or for 3 hours at room temperature or for 1 hour at 37° C.), with a mixture of four peptides prepared as described in a ratio by weight of II:IV:V:VI=1:0.25:1:1 at 3.25 ug per well of the mixture in 100 ul 10 mM NaHCO$_3$ buffer, pH 9.5. The wells were washed three times with phosphate buffered saline (PBS) and then incubated with 250 ul of 3% by weight of gelatin in PBS at 37° C. for 1 hour to block non-specific protein binding sites, followed by three more washes with PBS containing 0.05% by volume of Tween 20. The test sera (blood taken from human patients or normal individuals) were diluted with PBS containing 20% by volume normal goat serum, 1% by weight gelatin and 0.05% by volume Tween 20 at dilutions of 1:20, volume to volume, respectively. 200 ul of the diluted sera were added to each well and allowed to react for 1 hour at 37° C. The wells were then washed three times with 0.05% by volume Tween 20 in PBS in order to remove unbound antibodies. Horseradish peroxidase conjugated goat anti-human IgG was used as a second antibody tracer to bind with the HTLV antibody-antigen complex formed in positive wells. 100 ul of peroxidase labeled goat anti-human IgG at a dilution of 1:3000 in 1% by volume normal goat serum, 0.05% by volume Tween 20 in PBS was added to each well and incubated at 37° C. for another 15 minutes.

The wells were washed five times with 0.05% by volume Tween 20 in PBS to remove unbound antibody and reacted with 100 ul of the substrate mixture containing 0.04% by weight orthophenylenediamine (OPD) and 0.012% by volume hydrogen peroxide in sodium citrate buffer, pH 5.0. This substrate mixture was used to detect the peroxidase label by forming a colored product. Reactions were stopped by the addition of 100 ul of 1.0M H$_2$SO$_4$ and the absorbance measured using an ELISA reader at 492 nm (i.e. A$_{492}$). Assays were performed in duplicate with one dilution (1:20) of serum samples from normal individuals or from patients with diseases unrelated to HTLV infection used as negative controls. Absorbance readings greater than the cutoff value of A$_{492}$=A$_{492}$ value for normal control+0.1 (A$_{492}$ value for a reactive control), were taken as positive. The results are shown in Table I and FIG. 4.

TABLE I

Detection of Antibodies to HTLV by ELISA* Using a Mixture of Four Peptides as Solid Phase Immunoadsorbent

| Subject | No. Positive/ No. Tested* | Percent Positive |
| --- | --- | --- |
| 1. Patients (Lot 5) with ATL (HTLV Western Blot Positive) | 94/94 | 100 |
| 2. Patients (Lot 5) with ATL (HTLV Western Blot Negative) | 0/6 | 0 |
| 3. Patients with AIDS/ARC or known to be infected with HIV | 10/161 | 6 |
| 4. Normal Subjects | 0/200 | 0 |

*Assay was performed using sera at 1:20 (v/v) dilution with buffer.
Note:
Sera from patients with ATL were kindly provided by the Japanese Red Cross, sera from patients with AIDS ARC, Primary Immunodeficiency, Leukemia/Lymphomas were kindly provided by Dr. S. Gupta at the University of California at Irvine, Dr. D. M. Knowles at Columbia University, and Dr. F. D. Siegal at the Long Island Jewish Hospital.

The results in Table show that the ELISA test procedure according to the present invention with sera samples is very accurate and highly specific. No immunoreactivity was found in sera from normal subjects.

It is to be noted that in screening tests to exclude virus contaminated blood from blood banks, the criteria for defining positive reactions may be made more stringent if desired.

EXAMPLE 3

Detection of Antibodies to HTLV by an Agglutination Assay

The presently claimed HTLV peptides, synthesized according to the Merrifield solid phase method, were conjugated to bovine serum albumin (BSA) which had been derivatized with m-maleimidobenzoyl-N-hydroxysuccinimide ester (MBS), essentially as described by Fu-Tong Liu et al., in Biochemistry 18:690–697 (1979). To 0.32 ml. of a BSA solution (100 mg/ml in 0.01M phosphate buffer, pH 7.0) at room temperature was added 0.013 ml of an MBS solution (0.025 mg/ml in dimethylformamide). The amount of MBS added to the BSA solution can be varied according to the optimal molar ratio of BSA to MBS determined for a specific conjugate studied. The mixture was stirred at room temperature for 1 hour, after which it was centrifuged to remove any precipitated albumin. The clarified mixture was then subjected to gel filtration on Sephadex G-25 and the protein-containing fractions, as detected by their absorbance at 280 nm, were pooled and stored frozen at −70° C. until needed.

The peptides were dissolved in H$_2$O at 10 mg/ml. A predetermined amount of each peptide solution was added dropwise to the previously activated BSA-MBS solution and stirred at room temperature for 3 hours. The final peptide-BSA conjugates were separated from other free peptides by gel filtration or extensive dialysis. The ratio of peptide of BSA was determined by SDS-PAGE according to conventional methods.

In one example, conjugated peptide VI-BSA was then adsorbed to double aldehyde fixed human o erythrocytes at pH 4.0. The peptide-conjugate coated erythrocytes were then washed with PBS and incubated with 5% normal human serum-PBS solution. These processed cells were then used in an agglutination assay for the detection of HTLV antibodies in both serum and plasma specimens.

A total of 100 sera from patients with adult T cell leukemia were tested for antibodies to HTLV by (1) an enzyme immunoassay (EIA) employing HTLV-I vital lysate as the solid phase [DuPont's HTLV-I ELISA]; (2) the Western Blot (WB) analysis; (3) the above-described HTLV agglutination assay employing peptide VI-BSA conjugate as the solid phase.

The results are shown in Table II.

TABLE II

| | | Results | |
| --- | --- | --- | --- |
| WB | No. Tested | EIA | HTLV Agglutination Assay |
| + | 77 | + | 77 positive + |
| intdeterm. | 2 | + | 2 negative* |
| − | 21 | − | 21 negative |

*The two specimens that tested negative with the HTLV agglutination assay were found to have antibodies only to the p19 core protein of HTLV.

EXAMPLE 4

Simultaneous Detection of Antibodies to HTLV and HIV (1 and 2) by an Enzyme Immunoassay Employing a Mixture of Seven Chemically Synthesized Peptides A solution containing seven of the chemically synthesized peptides of the present invention was used to coat the wells of 96 well plates, according to the procedure of Example I.

Three of the peptides were derived from the HTLV-I peptide family [II, IV and VI]; three, from the HIV-1 peptide family [XIII, XIV and XV]; and one, from the HIV-2 peptide family [XVI]. The peptides II:IV::VI:XIII:XIV:XV:XVI were present at a ratio of 2:0.2:2:10:1:1:5 for a total concentration of 21.2 ug/ml. A total of 771 specimens from donors known to be HIV-1 positive (155 specimens); HIV-2 positive (10 specimens); HTLV positive by Wester Blot (92) specimens); HTLV negative by Western Blot (4 specimens); patients with autoimmune diseases (AI, 36 specimens); and, from random blood donors (RBD, 474 specimens), were tested on the peptide-coated plates for their respective retroviral immunoreactivies.

Figure 5:
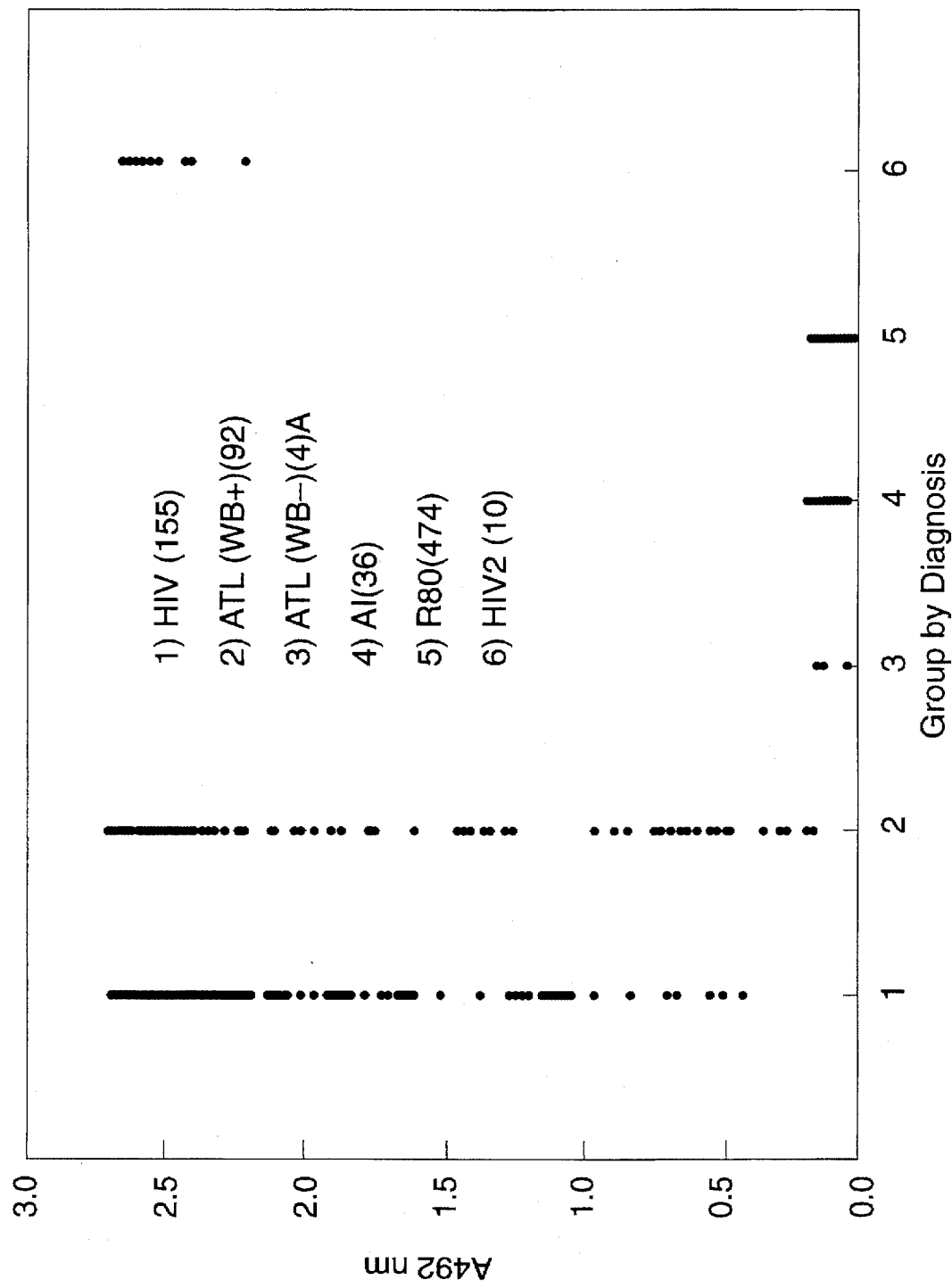
FIG. 5 is a histogram depicting the simultaneous detection of antibodies to HTLV-I and HIV (1 and 2) by an enzyme immunoassay employing a mixture of seven chemically synthesized peptides described herein.

Performance of this synthetic peptide-based retroviral-combo EIA (HTLV and HIV-1 and 2) with these specimens is illustrated in FIG. 5. The results clearly indicate the usefulness of these HTLV peptides in conjunction with the HIV peptides for the detection of retroviral infections.

EXAMPLE 5

Detection of Antibodies to HTLV by an Immunoradiometric Assay (IRMA)

Wells of 96-well flexible-polyvinylchloride (PVC) plates are coated at 4° C. overnight (or 3 hours at room temperature) with a mixture (1:1:1) of these three peptides, prepared as described, at 1.5 ug per well in 100 ul 10 mM $NaHCO_3$ suffer, pH 9.5. The wells are washed three times with phosphate buffered saline (PBS) and then incubated with 250 ul of 3% by weight gelatin in PBS at 37° C. for 1 hour to block non-specific protein binding sites, followed by three more washes with PBS containing 0.05% by volume Tween 20. The test sera (blood taken from a human patient or normal individual) are diluted with PBS containing 20% by volume normal goat serum, 1% by weight gelatin 9 and 0.05% by volume Tween 20 at dilutions of 1:20 and 1:200 (volume to volume) respectively. 200 ul of the diluted sera are added to each cell and allowed to react for 1 hour at 37° C. The wells are then washed three times with 0.05% by volume Tween 20 in PBS in order to remove unbound antibodies. I-125 labeled affinity purified goat anti-human IgG is used as a second antibody purified goat anti-human IgG of 50,000–200,000 cpm in 1% by volume normal goat serum, 0.05% by volume Tween 20 in PBS is added to each well and incubated at 37° C. for another hour.

The wells was washed five times with 0.05% by volume Tween 20 in PBS to remove unbound second antibody and dried. The wells are cut and counted by a gamma-scintillation counter. Assays are performed in duplicate with a 1:20 dilution volume to volume. Normal sera sample is negative controls are also tested simultaneously. Cpm readings greater than the average readings of normal sera samples+4SD (standard deviation) are taken as positive.

EXAMPLE 6

Detection Of Antibodies To HTLV By An Agglutination Assay Utilizing As The Solid Phase Immunoadsorbent Gelatin Particles, Erythrocytes Of Different Animal Species, Or Latex Beads Coated With A Mixture Of Peptides One ml thoroughly washed erythrocytes, gelatin particles, or polystyrene latex beads are coated with the peptide mixture at concentration in the range of 5 ug/ml to 1 mg/ml. The peptide mixture coated cells, particles or beads are then incubated with serially diluted serum samples in the wells of a 96-well U-shaped microplate or on a slide. After being left at room temperature for about an hour, the settled agglutination patterns on the bottom of the wells or on the slide are read, and the largest dilution showing a positive reaction is recorded.

This is a one-step assay which could be used for both qualitative and quantitative analysis for the presence of antibodies to HTLV in specimens including sera or biofluids.

EXAMPLE 7

A third test kit for detecting HTLV antibodies using the agglutination assay comprises a compartmented enclosure containing multiple microwell plates and other accessory materials for an agglutination assay including (1) a bottle of peptide mixture coated erythrocytes, gelatin particles or latex polystyrene beads; (2) normal human serum (as a negative control); and, (3) NP40 treated and heat inactivated, HTLV-I seropositive serum (as a positive control), and (4) specimen diluent. The procedure described in Example 3 is to be followed.

EXAMPLE 8

A diagnostic test kit for the detection of HTLV antibodies can be constructed. The test kit comprises a compartmented enclosure containing multiple 96-well plates coated prior to use with the peptide(s) or peptide mixture(s) of the present invention in 100 ul pH 9.5 10 mM $NaHCO_3$ buffer. The kit further comprises materials for enzyme detection in separate sealed containers consisting of: 1) normal human serum (as a negative control); 2) NP40 treated and heat inactivated, HTLV-I seropositive serum (as a positive control); 3) specimen diluent; 4) peroxidase labeled-goat antihuman IgG; and 5) a color change indicator consisting of, for example, orthophenylenediamine (OPD) and hydrogen peroxide in phosphate citrate buffer. The procedure described in Example I is to be followed.

In this test, 96-well plates, precoated with a peptide or peptide mixture of the present invention, can be replaced by polystyrene beads, or multiple mini-columns filled with controlled pore size glass beads, or nitrocellulose paper strips precoated with the peptides of the present invention for use as the solid phase immunoabsorbent.

EXAMPLE 9

A second test kit for detecting antibodies using the immunoradiometric assay (IRMA) comprises a compartmented enclosure containing multiple 96-well bendable polyvinychloride (PVC) plates precoated with the peptide(s) or peptide mixture(s) according to the present invention in 100 ul of pH 9.5 10 mM $NaHCO_3$ buffer and materials for radioimmunoassay including: 1) normal human serum (as a negative control); 2) NP40 treated and heat inactivated, HTLV-1 seropositive serum (as a positive control); 3) specimen diluent; and, 4) I-125 labeled goated anti human IgG. The procedure described in Example 5 is to be followed.

In this test kit, 96-well PVC plates precoated with the peptides of the present invention can be replaced by polystyrene beads precoated with the peptide of the present invention for use as the solid phase immunoadsorbent.

EXAMPLE 10

Specific Detection of Antibodies to HTLV-I and not HTLV-II By An Enzyme Immunoassay Employing A Synthesized Peptide A solution containing the synthesized HTLV-I peptide (IV) of the present invention at 5ug/ml having the sequence corresponding to HTLV-I, APPLLPHSNLDHILEPSIPWKSKLLTLVQLTLQS, SEQ ID NO: 4 was used to coat the wells of 96 well plates, according to the procedure of Example 1. A total of 120 specimens from blood donors or individuals known to be repeat reactive on an HTLV lysate based test were tested on the peptide-coated plates for their immunoreactivity. Of the 120 samples, 73 had also been tested by polymerase chain reaction with HTLV-I or HTLV-II specific DNA probes (PCR). Of these, 43 were positive for HTLV-I by PCR and 30 were positive for HTLV-II by PCR. Supplemental testings, such as Western Blot and radioimmunoprecipitation assay (RIPA), were also performed on all 120 samples. For those samples with no PCR results available, the WB and RIPA results were considered as probably HTLV-1 or HTLV-II positive. The 120 samples thus comprised the following categories: HTLV-I positive by PCR (43 specimens); probably HTLV-I positive by Western Blot and RIPA (12 specimens); HTLV-II positive by PCR (30 specimens); probably HTLV-II positive by Western Blot and RIPA (26 specimens); and repeat reactive for HTLV by vital lysate ELISA, but negative by Western Blot and negative by RIPA (RR (WB NEG), 9 specimens).

Performance of this synthetic peptide-based EIA (HTLV-I specific) is presented in Table III. The results in Table III show that the method is highly sensitive and specific for HTLV-I and that it can be used to distinguish HTLV-II from HTLV-I infection. The whole virus lysate EIA, on the other hand, does not distinguish between the two vital infections since it gave positive results for all 120 sample.

TABLE III

TESTED BY PEPTIDE IV

| Subject (confirmed by) | No. Positive/ No. Tested | Percent Positive |
|---|---|---|
| 1. HTLV-I (PCR) | 41/43 | 95.3 |
| 2. HTLV-I (WB/RIPA) | 12/12 | 100 |
| 3. HTLV-II (PCR) | 4/30 | 13.3 |
| 4. HTLV-II (WB/RIPA) | 1/26 | 3.8 |
| 5. RR (WB NEG) | 0/9 | 0 |

Sera from blood donors and individuals known to be HTLV-I or HTLV-II positive, confirmed either by PCR, RIPA or WB, were kindly provided by Serologicals, Inc. and by Dr. Chang Fang of the American Red Cross (ARC).

EXAMPLE 11

Specific Detection of Antibodies to HTLV-II and not HTLV-I By An Enzyme Immunoassay Employing A Synthesized Peptide A solution containing a synthetic peptide analogue of the HTLV-I peptide IV of the present invention, designated as HTLV-II peptide X, having the sequence corresponding to HTLV-II in FIG. 2, i.e., with an amino acid sequence of SPPLVHDSDLEHVLTPSTSWTTKILKFIQLTLQS, SEQ ID NO: 10 was used at a concentration of 5 ug/ml to coat the wells of 96 well plates, according to the procedure of Example 1. The same 120 specimens as in Example 10 were tested.

Performance of this synthetic peptide-based EIA (HTLV-II specific) is presented in Table IV. The results in Table IV show that the method is highly sensitive and specific for HTLV-II and that it can be used to distinguish antibodies against HTLV-II from antibodies against HTLV-I. The whole virus lysate EIA, on the other hand, does not distinguish between the two viral infection since it gave positive results for all 120 samples.

TABLE IV

TESTED BY PEPTIDE X

| Subject (confirmed by) | No. Positive/ No. Tested | Percent Positive |
|---|---|---|
| 1. HTLV-II (PCR) | 28/30 | 93.3 |
| 2. HTLV-II (WB/RIPA) | 24/26 | 92.3 |
| 3. HTLV-I (PCR) | 0/43 | 0 |
| 4. HTLV-I (WB/RIPA) | 0/12 | 0 |
| 5. RR (WB NEG) | 0/9 | 0 |

EXAMPLE 12

Two peptides were synthesized to have amino acid sequences which correspond to segments of APPLLPHSNLDHILEPSIPWKSKLLTLVQLTLQS SEQ ID NO: 4 (IV) AND SPPLVHDSDLEHVLTPSTSWTTKILKFIQLTLQS (V). The sequence of the peptide segments are as follows:

APPLLPHSNLDHILEPSIPWKSKLLTLVQLTLQS SEQ ID N(IV)

PHSNLDHILEPSIPWKSKLLTLVQLTLQS SEQ ID NO: 17 (IVA)

SPPLVHDSDLEHVLTPSTSWTTKILKFIQLTLQS SEQ ID NO: 10 (X)(V)

HDSDLEHVLTPSTSWTTKILKFIQLTLQS SEQ ID NO(XA)(VA)

The synthesized peptides were used in an ELISA against sera which have been found to be positive for antibodies to HTLV-I and HTLV-II. The procedure described in Example 1 of the above identified patent application was followed.

The results in absorbance at 492 nm ($A_{492\ nm}$) obtained are tabulated below.

TABLE V

| | IV | IVA | X | XA |
|---|---|---|---|---|
| BG* | 0.004 | −0.001 | −0.008 | 0.002 |
| NRC** | 0.017 | 0.010 | 0.069 | 0.046 |
| HTLV(+), sera | | | | |
| 9-301 | 2.239 | 1.682 | 0.281 | 0.292 |
| 9-302 | 0.738 | 0.545 | 0.065 | 0.091 |
| 9-307 | 4.030 | 3.462 | 0.084 | 0.159 |
| 9-310 | 0.145 | 0.053 | 0.187 | 0.095 |
| 9-312 | 2.499 | 3.329 | 0.051 | 0.040 |
| 9-321 | 0.391 | 0.521 | 0.143 | 0.165 |
| 9-326 | 2.641 | 1.215 | 0.090 | 0.096 |
| 9-329 | 4.030 | 3.365 | 0.077 | 0.074 |
| 9-317 | 0.017 | 0.069 | 3.862 | 0.211 |
| 9-323 | 0.025 | 0.287 | 0.335 | 0.100 |
| 9-350 | 0.010 | 0.517 | 2.713 | 0.013 |
| 9-352 | 0.012 | 0.168 | 0.993 | 0.278 |
| 9-357 | 0.022 | 0.683 | 2.699 | 0.187 |
| 9-359 | 0.037 | 0.064 | 1.187 | 0.259 |
| 9-362 | 0.057 | 0.202 | 0.828 | 0.101 |
| 9-364 | 0.046 | 0.177 | 0.539 | 0.212 |

*BG = blank
**NRC = Non-Reactive Control

The results show that segments of peptides (IV) and (V) are immunoreactive to HTLV-I and/or HTLV-II antibodies. The $A_{492\ nm}$ readings (underlined) show that Peptides IrA and VA are more immunoreactive than Peptides IV and V respectively in some instances.

EXAMPLE 13

A segment of peptide (IV) having the following amino acid sequence was synthesized:

APPLLPHSNLDHILEPSIPWK (IVB)

This segment peptide (IVB) and peptide (IV) were also tested in accordance with Example 1 of the above identified patent application in an ELISA assay using HTLV-I positive sera and the results compared in Table II. The results showed that peptide (IVB) is immunoreactive to antibodies to HTLV.

TABLE VI

|  | Peptide IV $A_{492nm}$ | Peptide IVB $A_{492nm}$ |
|---|---|---|
| BG | 0.043 | 0.040 |
| NRC | 0.026 | 0.031 |
| HTLV(+), sera | | |
| 9-301 | 1.487 | 2.323 |
| 9-302 | 0.379 | 0.418 |
| 9-307 | 3.065 | 3.309 |
| 9-310 | 0.461 | 0.406 |
| 9-312 | 1.430 | 1.167 |
| 9-321 | 0.268 | 0.371 |
| 9-326 | 1.701 | 1.645 |
| 9-329 | 3.392 | 3.092 |
| 9-330 | 0.004 | 0.012 |
| 9-334 | 0.039 | 0.040 |
| 9-339 | 0.321 | 0.352 |
| 9-341 | 0.321 | 0.460 |
| 9-342 | 0.430 | 0.552 |
| 9-345 | 0.309 | 0.394 |
| 9-361 | 1.251 | 2.139 |
| 9-363 | 0.023 | 0.025 |
| 9-374 | 3.245 | 3.494 |
| 9-367 | 2.100 | 2.473 |

The $A_{492\ nm}$ readings (underlined) showed that Peptide IVB has higher immunoreactivity than the corresponding Peptide IV in some instances.

EXAMPLE 14

Octameric peptides (IV) and (V) on a branching lysine core polymer were synthesized and tested in accordance with Example 1 of the above identified patent application in an ELISA against HTLV-I and HTLV-II positive sera, respectively.

The results obtained were:

TABLE VII

| | Peptide IV | Octameric IV | | Peptide X | Octameric X |
|---|---|---|---|---|---|
| BL | 0.042 | 0.039 | BL | 0.055 | 0.046 |
| NRC HTLV-I(+) Sera code | 0.027 | 0.082 | NRC HTLV-I(+) Sera code | 0.035 | 0.096 |
| 9-301 | 2.329 | 3.451 | 9-317 | 3.862 | 3.620 |
| 9-302 | 0.738 | 2.681 | 9-323 | 0.335 | 0.561 |
| 9-307 | 4.000 | 3.113 | 9-350 | 2.713 | 2.455 |
| 9-310 | 0.145 | 1.111 | 9-352 | 0.993 | 1.058 |
| 9-312 | 2.499 | 3.375 | 9-357 | 2.699 | 3.170 |
| 9-321 | 0.391 | 1.498 | 9-359 | 1.187 | 1.532 |
| 9-326 | 2.993 | 3.388 | 9-362 | 0.828 | 0.574 |
| 9-329 | 3.140 | 3.355 | 9-364 | 0.539 | 0.791 |
| 9-339 | 0.624 | 2.467 | | | |
| 9-341 | 1.351 | 3.495 | | | |
| 9-342 | 1.272 | 3.181 | | | |
| 9-345 | 0.591 | 0.941 | | | |
| 9-361 | 1.050 | 3.217 | | | |
| 9-363 | 0.043 | 0.038 | | | |
| 9-374 | 3.346 | 3.212 | | | |
| 9-397 | 3.315 | 2.657 | | | |

TABLE VII-continued

| | Peptide IV | Octameric IV | | Peptide X | Octameric X |
|---|---|---|---|---|---|
| Relative Immunoreactivity | 100% | 143.7% | | 100% | 105% |

The A492 nm readings (underlined) indicate higher immunoreactivity of the octameric peptides than their corresponding parent peptides IV and X. The results also show that polymers of Peptides IV and X are immunoreactive.

EXAMPLE 15

SYNTHESIS OF OCTAMERIC HTLV PEPTIDE ANTIGENS AS KEY COMPONENTS OF IMMUNOGENS/VACCINES

The use of a limited sequential propagation of a trifunctional amino acid (or similar analogues) to form a core that serves as a low molecular weight matrix is the basic underlying principle for the formation of a radially branching multimerit peptide antigen system. The trifunctional amino acid, Boc-Lys(Boc), or di-(Boc)-Lys is most suitable since both N-a and N-e amino acid groups are available as reactive ends.

An octameric heptalysyl core resin was prepared by coupling di-t-Boc Lys onto an extra low loading 0.14 mmole/g MBHA (4-methyl benzhydrylamine) resin on a Biosearch 9500 instrument. During each of the two coupling cycles, di-(Boc)-Lys was used for single coupling followed by two capping reactions (with 0.3M acetylimidazole in DMF dimethylformamide).

After two additional di-(Boc)-Lys couplings onto the first di-($NH_2$) Lys-resin, the substitution level of synthetic octameric resin was determined by ninhydrin test and found to be in the range as calculated based on a theoretical coupling yield. The resin was used thereafter for the synthesis of octameric peptide immunogens.

Acid-labile tert-butyloxycarbonyl (y-Boc) was used for the protection of N-a amino acid. The following functional side-chain protecting groups were used: O-benzyl for Thr, Ser, Glu and Tyr; N-tosyl for Arg; BOM (i.e. Boc-$N^{im}$-Benzyloxymethyl-) for His; N-dichlorobenzyl- oxycarbonyl for Lys; S-4-methylbenzyl- for Cys; O-cyclohexyl for Asp and CHO for Trp. Successive amino acids were added for the synthesis of octameric HTLV-1 envelope peptide according to the sequence APPLLPHSNLDHILEPSIPWK-SKLLTLVQLTLQS SEQ ID NO: 4 (IV) and octameric HTLV-II envelope peptide according to the sequence of SPPLVHDSDLEHVLTDSTSWITKILKFIQLTLQS SEQ ID NO: 10 (X). The resultant octameric peptidyl resin for each of the synthesis was cleaved by anhydrous HF. The released octameric antigen was extracted by acetic acid, 8 after two cycles of either washings of the cleaved peptidyl resin, and lyophilized to dryness so as to be ready for use as an immunogen.

These HTLV-I/II octameric peptides were injected individually and as a mixture into healthy, naive animals (guinea pigs and rabbits) both intramuscularly and subcutaneously at a dosage of 100 ug peptide in complete/incomplete Freund's adjuvant. After the initial immunization, these animals were boosted at the same dose at 3, 6 and 32 weeks. The animals were bled monthly and the collected immune sera were tested for their anti-HTLV-I/II envelope peptide immunoreactivity by enzyme immunoassays as shown in Table VIII. Six months after the last boost, the immunized rabbits were challenged by experimental inoculation with HTLV-I or HTLV-II infected cells to evaluate the efficacy in using a mixture of these octameric envelope peptides as a vaccine for the prevention of HTLV infection.

TABLE VIII

| | | Coating Antigen (5 ug/mL @ 0.1 mL per well) O.D. 492 nm EIA | | | |
|---|---|---|---|---|---|
| a HTLV-I (Octa IV) | | 1:10² | HTLV-I 1:10³ | (Monomeric IV) 1:10⁴ | 1:10⁵ |
| Prebleed Control | (0 wpi) | 0.013 | | | |
| G.p.A | 3 wpi | 3.563 | 3.626 | 2.074 | 0.171 |
| G.p.A | 12 wpi | 3.396 | 3.638 | 2.976 | 0.580 |
| G.p.A | 21 wpi | 3.571 | 3.607 | 1.743 | N.D. |
| a HTLV-II (Octa X) | | 1:10² | HTLV-I 1:10³ | (Monomeric X) 1:10⁴ | 1:10⁵ |
| Prebleed Control | (0 wpi) | 0.000 | | | |
| G.p.A | 9 wpi | 3.543 | 3.699 | 3.311 | 0.583 |
| G.p.A | 12 wpi | 3.378 | 3.173 | 2.476 | 0.376 |

Representative data points from immunized guinea pigs A and B bled over a three to five months period as shown in Table VIII indicated that high titers of anti-HTLV-I envelop peptide (IV) or anti-HTLV-II envelope peptide (X) reactivity were obtained from as early as three weeks after immunizations and the titers remained high throughout the five months period, evidence of strong immunogenicity of the octameric HTLV immunogens (IV and X), thus their efficacious nature as key components in a vaccine.

It is to be understood that the above examples are illustrative of the present invention and are not meant to limit the scope thereof.

What is claimed is:

1. A peptide composition comprising a peptide selected from the group consisting:

$$Y_a\text{-}AA_6\text{-}AA_{21}\text{-}B_a\text{-}Z \quad \text{(iv)}$$

wherein $Y_a$ is $AA_1\text{-}AA_5$ and $B_a$ is $AA_{22}\text{-}AA_{34}$ and $AA_1\text{-}AA_{34}$ is APPLLPHSNLDHILEPSIPWK-SKLLTLVQLTLQS (SEQ ID NO:4) (IV), and Z is —OH or —NH$_2$;

an analogue of the peptide having an amino acid sequence derived from a strain/isolate of HTLV in a region corresponding to the peptide;

a conjugate of the peptide or its analogue with carrier proteins; and a polymer of the peptide or its analogue.

2. A peptide according to claim 1 having the sequence:

APPLLPHSNLDHILEPSIPWKSKLLTLVQLTLQS-Z (SEQ ID NO:4)     (IV).

3. An analogue of peptide (iv) according to claim 1 having the amino acid sequence:

$$Y_a{'}\text{-}AA_6\text{-}AA_{21}\text{-}B_a{'}\text{-}Z \quad (x)$$

wherein $Y_a{'}$ is $AA_1\text{-}AA_5$ and $B_a{'}$ is $AA_{22}\text{-}AA_{34}$; $AA_1\text{-}AA_{34}$ is SPPLVHDSDLEHVLTPSTSWTTKILKFIQLTLQS (SEQ ID NO:10) (X), and Z is —OH or —NH$_2$.

* * * * *

SEQUENCE LISTING ( 1 ) GENERAL INFORMATION:

( i i i ) NUMBER OF SEQUENCES: 19

( 2 ) INFORMATION FOR SEQ ID NO:1:

( i ) SEQUENCE CHARACTERISTICS:
        ( A ) LENGTH: 20
        ( B ) TYPE: Amino acid
        ( C ) STRANDEDNESS: Single
        ( D ) TOPOLOGY: Unknown ( i i ) MOLECULE TYPE: Peptide ( x i ) SEQUENCE DESCRIPTION: SEQ ID NO:1:

```
Gly Leu Asp Leu Leu Phe Trp Glu Gln Gly Gly Leu Cys Lys Ala
 1               5                  10                  15

Leu Gln Glu Gln Cys
                20
```

( 2 ) INFORMATION FOR SEQ ID NO:2:

( i ) SEQUENCE CHARACTERISTICS:
        ( A ) LENGTH: 24
        ( B ) TYPE: Amino acid
        ( C ) STRANDEDNESS: Single
        ( D ) TOPOLOGY: Unknown ( i i ) MOLECULE TYPE: Peptide ( x i ) SEQUENCE DESCRIPTION: SEQ ID NO:2:

```
Gln Asn Arg Arg Gly Leu Asp Leu Leu Phe Trp Glu Gln Gly Gly
 1               5                  10                  15

Leu Cys Lys Ala Leu Gln Glu Gln Cys
                20
```

( 2 ) INFORMATION FOR SEQ ID NO:3:

( i ) SEQUENCE CHARACTERISTICS:
        ( A ) LENGTH: 16

(B) TYPE: Amino acid
(C) STRANDEDNESS: Single
(D) TOPOLOGY: Unknown (ii) MOLECULE TYPE: Peptide (xi) SEQUENCE DESCRIPTION: SEQ ID NO:3:

```
Asn Arg Arg Gly Leu Asp Leu Leu Phe Trp Glu Gln Gly Gly Leu
 1               5                  10                      15
Cys
```

(2) INFORMATION FOR SEQ ID NO:4:

(i) SEQUENCE CHARACTERISTICS:
(A) LENGTH: 34
(B) TYPE: Amino acid
(C) STRANDEDNESS: Single
(D) TOPOLOGY: Unknown (ii) MOLECULE TYPE: Peptide (xi) SEQUENCE DESCRIPTION: SEQ ID NO:4:

```
Ala Pro Pro Leu Leu Pro His Ser Asn Leu Asp His Ile Leu Glu
 1               5                  10                      15
Pro Ser Ile Pro Trp Lys Ser Lys Leu Leu Thr Leu Val Gln Leu
                20                  25                      30
Thr Leu Gln Ser
```

(2) INFORMATION FOR SEQ ID NO:5:

(i) SEQUENCE CHARACTERISTICS:
(A) LENGTH: 40
(B) TYPE: Amino acid
(C) STRANDEDNESS: Single
(D) TOPOLOGY: Unknown (ii) MOLECULE TYPE: Peptide (xi) SEQUENCE DESCRIPTION: SEQ ID NO:5:

```
Ser Ser Thr Pro Leu Leu Tyr Pro Ser Leu Ala Leu Pro Ala Pro
 1               5                  10                      15
His Leu Thr Leu Pro Phe Asn Trp Thr His Cys Phe Asp Pro Gln
                20                  25                      30
Ile Gln Ala Ile Val Ser Ser Pro Cys His
                35                  40
```

(2) INFORMATION FOR SEQ ID NO:6:

(i) SEQUENCE CHARACTERISTICS:
(A) LENGTH: 38
(B) TYPE: Amino acid
(C) STRANDEDNESS: Single
(D) TOPOLOGY: Unknown (ii) MOLECULE TYPE: Peptide (xi) SEQUENCE DESCRIPTION: SEQ ID NO:6:

```
Cys Phe Asp Pro Gln Ile Gln Ala Ile Val Ser Ser Pro Cys His
 1               5                  10                      15
Asn Ser Leu Ile Leu Pro Pro Phe Ser Leu Ser Pro Val Pro Thr
                20                  25                      30
Leu Gly Ser Arg Ser Arg Arg Ala
                35
```

(2) INFORMATION FOR SEQ ID NO:7:

( i ) SEQUENCE CHARACTERISTICS:
    ( A ) LENGTH: 20
    ( B ) TYPE: Amino acid
    ( C ) STRANDEDNESS: Single
    ( D ) TOPOLOGY: Unknown ( i i ) MOLECULE TYPE: Peptide ( x i ) SEQUENCE DESCRIPTION: SEQ ID NO:7:

```
Gly  Leu  Asp  Leu  Leu  Phe  Trp  Glu  Gln  Gly  Gly  Leu  Cys  Lys  Ala
 1              5                        10                        15

Ile  Gln  Glu  Gln  Cys
              20
```

( 2 ) INFORMATION FOR SEQ ID NO:8:

( i ) SEQUENCE CHARACTERISTICS:
        ( A ) LENGTH: 24
        ( B ) TYPE: Amino acid
        ( C ) STRANDEDNESS: Single
        ( D ) TOPOLOGY: Unknown ( i i ) MOLECULE TYPE: Peptide ( x i ) SEQUENCE DESCRIPTION:SEQ ID NO:8:

```
Gln  Asn  Arg  Arg  Gly  Leu  Asp  Leu  Leu  Phe  Trp  Glu  Gln  Gly  Gly
 1              5                        10                        15

Leu  Cys  Lys  Ala  Ile  Gln  Glu  Gln  Cys
                    20
```

( 2 ) INFORMATION FOR SEQ ID NO:9:

( i ) SEQUENCE CHARACTERISTICS:
        ( A ) LENGTH: 16
        ( B ) TYPE: Amino acid
        ( C ) STRANDEDNESS: Single
        ( D ) TOPOLOGY: Unknown ( i i ) MOLECULE TYPE: Peptide ( x i ) SEQUENCE DESCRIPTION:SEQ ID NO:9:

```
Asn  Arg  Arg  Gly  Leu  Asp  Leu  Leu  Phe  Trp  Glu  Gln  Gly  Gly  Leu
 1              5                        10                        15

Cys
```

( 2 ) INFORMATION FOR SEQ ID NO:10:

( i ) SEQUENCE CHARACTERISTICS:
        ( A ) LENGTH: 34
        ( B ) TYPE: Amino acid
        ( C ) STRANDEDNESS: Single
        ( D ) TOPOLOGY: Unknown ( i i ) MOLECULE TYPE: Peptide ( x i ) SEQUENCE DESCRIPTION:SEQ ID NO:10:

```
Ser  Pro  Pro  Leu  Val  His  Asp  Ser  Asp  Leu  Glu  His  Val  Leu  Thr
 1              5                        10                        15

Pro  Ser  Thr  Ser  Trp  Thr  Thr  Lys  Ile  Leu  Lys  Phe  Ile  Gln  Leu
                    20                       25                       30

Thr  Leu  Gln  Ser
```

( 2 ) INFORMATION FOR SEQ ID NO:11:

( i ) SEQUENCE CHARACTERISTICS:
        ( A ) LENGTH: 30

(B) TYPE: Amino acid
(C) STRANDEDNESS: Single
(D) TOPOLOGY: Unknown (ii) MOLECULE TYPE: Peptide (xi) SEQUENCE DESCRIPTION:SEQ ID NO:11:

| Ser | Ser | Arg | Thr | Ile | Leu | Phe | Pro | Ser | Leu | Ala | Leu | Pro | Ala | Pro |
|---|---|---|---|---|---|---|---|---|---|---|---|---|---|---|
| 1 | | | | 5 | | | | | 10 | | | | | 15 |

| Pro | Ser | Gln | Pro | Arg | Leu | Gln | Ala | Ile | Thr | Thr | Asp | Asn | Cys | Asn |
|---|---|---|---|---|---|---|---|---|---|---|---|---|---|---|
| | | | | 20 | | | | | 25 | | | | | 30 |

(2) INFORMATION FOR SEQ ID NO:12:

(i) SEQUENCE CHARACTERISTICS:
        (A) LENGTH: 37
        (B) TYPE: Amino acid
        (C) STRANDEDNESS: Single
        (D) TOPOLOGY: Unknown (ii) MOLECULE TYPE: Peptide (xi) SEQUENCE DESCRIPTION:SEQ ID NO:12:

| Cys | Tyr | Gln | Pro | Arg | Leu | Gln | Ala | Ile | Thr | Thr | Asp | Asn | Cys | Asn |
|---|---|---|---|---|---|---|---|---|---|---|---|---|---|---|
| 1 | | | | 5 | | | | | 10 | | | | | 15 |

| Asn | Ser | Ile | Ile | Leu | Pro | Pro | Phe | Ser | Leu | Ala | Pro | Val | Pro | Leu |
|---|---|---|---|---|---|---|---|---|---|---|---|---|---|---|
| | | | | 20 | | | | | 25 | | | | | 30 |

| Ala | Thr | Arg | Arg | Arg | Arg | Ala |
|---|---|---|---|---|---|---|
| | | | | 35 | | |

(2) INFORMATION FOR SEQ ID NO:13:

(i) SEQUENCE CHARACTERISTICS:
        (A) LENGTH: 21
        (B) TYPE: Amino acid
        (C) STRANDEDNESS: Single
        (D) TOPOLOGY: Unknown (ii) MOLECULE TYPE: Peptide (xi) SEQUENCE DESCRIPTION:SEQ ID NO:13:

| Arg | Ile | Leu | Ala | Val | Glu | Arg | Tyr | Leu | Lys | Asp | Gln | Gln | Leu | Leu |
|---|---|---|---|---|---|---|---|---|---|---|---|---|---|---|
| 1 | | | | 5 | | | | | 10 | | | | | 15 |

| Gly | Ile | Trp | Gly | Cys | Ser |
|---|---|---|---|---|---|
| | | | | 20 | |

(2) INFORMATION FOR SEQ ID NO:14:

(i) SEQUENCE CHARACTERISTICS:
        (A) LENGTH: 19
        (B) TYPE: Amino acid
        (C) STRANDEDNESS: Single
        (D) TOPOLOGY: Unknown (ii) MOLECULE TYPE: Peptide (xi) SEQUENCE DESCRIPTION:SEQ ID NO:14:

| Ile | Trp | Gly | Cys | Ser | Gly | Lys | Leu | Ile | Cys | Thr | Thr | Ala | Val | Pro |
|---|---|---|---|---|---|---|---|---|---|---|---|---|---|---|
| 1 | | | | 5 | | | | | 10 | | | | | 15 |

| Trp | Asn | Ala | Ser |
|---|---|---|---|

(2) INFORMATION FOR SEQ ID NO:15:

(i) SEQUENCE CHARACTERISTICS:
        (A) LENGTH: 11
        (B) TYPE: Amino acid
        (C) STRANDEDNESS: Single ( D ) TOPOLOGY: Unknown ( i i ) MOLECULE TYPE: Peptide ( x i ) SEQUENCE DESCRIPTION:SEQ ID NO:15:

Ile Val Arg Met Tyr Ser Pro Thr Ser Ile Leu
 1               5                   10

( 2 ) INFORMATION FOR SEQ ID NO:16:

( i ) SEQUENCE CHARACTERISTICS:
          ( A ) LENGTH: 16
          ( B ) TYPE: Amino acid
          ( C ) STRANDEDNESS: Single
          ( D ) TOPOLOGY: Unknown ( i i ) MOLECULE TYPE: Peptide ( x i ) SEQUENCE DESCRIPTION:SEQ ID NO:16:

Asp Gln Ala Arg Leu Asn Ser Trp Gly Cys Ala Phe Arg Gln Val
 1               5                   10                  15
Cys ( 2 ) INFORMATION FOR SEQ ID NO:17:

( i ) SEQUENCE CHARACTERISTICS:
          ( A ) LENGTH: 28
          ( B ) TYPE: Amino acid
          ( C ) STRANDEDNESS: Single
          ( D ) TOPOLOGY: Unknown ( i i ) MOLECULE TYPE: Peptide ( x i ) SEQUENCE DESCRIPTION:SEQ ID NO:17:

Pro His Ser Asn Leu Asp His Ile Leu Glu Pro Ser Ile Pro Trp
 1               5                   10                  15
Lys Ser Lys Leu Leu Thr Leu Val Gln Thr Leu Gln Ser
                20                  25

( 2 ) INFORMATION FOR SEQ ID NO:18:

( i ) SEQUENCE CHARACTERISTICS:
          ( A ) LENGTH: 29
          ( B ) TYPE: Amino acid
          ( C ) STRANDEDNESS: Single
          ( D ) TOPOLOGY: Unknown ( i i ) MOLECULE TYPE: Peptide ( x i ) SEQUENCE DESCRIPTION:SEQ ID NO:18:

His Asp Ser Asp Leu Glu His Val Leu Thr Pro Ser Thr Ser Trp
 1               5                   10                  15
Thr Thr Lys Ile Leu Lys Phe Ile Gln Leu Thr Leu Gln Ser
                20                  25

( 2 ) INFORMATION FOR SEQ ID NO:19:

( i ) SEQUENCE CHARACTERISTICS:
          ( A ) LENGTH: 21
          ( B ) TYPE: Amino acid
          ( C ) STRANDEDNESS: Single
          ( D ) TOPOLOGY: Unknown ( i i ) MOLECULE TYPE: Peptide ( x i ) SEQUENCE DESCRIPTION:SEQ ID NO:19:

Ala Pro Pro Leu Leu Pro His Ser Asn Leu Asp His Ile Leu Gly
 1               5                   10                  15

```
Pro Ser Ile Pro Trp Lys
                20
```